United States Patent [19]

Umezawa et al.

[11] 4,298,727
[45] Nov. 3, 1981

[54] 3',4'-DIDEOXYKANAMYCIN A AND 1-N-(S)-α-HYDROXY-ω-AMINOALKANOYL) DERIVATIVES THEREOF

[75] Inventors: Hamao Umezawa; Sumio Umezawa, both of Tokyo; Tsutomu Tsuchiya, Yokohama; Tomo Jikahara; Toshiaki Miyake, both of Kawasaki, all of Japan

[73] Assignee: Zaidan Hojin Biseibutsu Kagaku KenkyuKai, Tokyo, Japan

[21] Appl. No.: 114,779

[22] Filed: Jan. 23, 1980

[30] Foreign Application Priority Data

Feb. 5, 1979 [JP] Japan .................................. 54-11402

[51] Int. Cl.³ .......................................... C07H 15/22
[52] U.S. Cl. ...................................... 536/10; 424/180; 424/181
[58] Field of Search .......................................... 536/10

[56] References Cited

U.S. PATENT DOCUMENTS

| Re. 28,647 | 12/1975 | Umezawa et al. | 536/10 |
|---|---|---|---|
| 2,931,798 | 5/1960 | Umezawa et al. | 536/10 |
| 3,781,268 | 12/1973 | Kawaguchi et al. | 536/10 |
| 3,886,139 | 5/1975 | Naito et al. | 536/10 |
| 3,904,597 | 9/1975 | Naito et al. | 536/10 |
| 3,925,353 | 12/1975 | Umezawa et al. | 536/10 |
| 4,001,208 | 1/1977 | Umezawa et al. | 536/10 |
| 4,104,372 | 8/1978 | Umezawa et al. | 536/10 |
| 4,107,424 | 8/1978 | Umezawa et al. | 536/10 |
| 4,120,955 | 10/1978 | Umezawa et al. | 536/10 |
| 4,147,861 | 4/1979 | Umezawa et al. | 536/10 |
| 4,156,078 | 5/1979 | Umezawa et al. | 536/10 |
| 4,169,939 | 10/1979 | Umezawa et al. | 536/10 |
| 4,170,642 | 10/1979 | Umezawa et al. | 536/10 |

OTHER PUBLICATIONS

Okamoto et al., "Science", vol. 157, pp. 1559-1561, 1967.
Woo et al., "Tetrahedron Letters", No. 28, pp. 2617-2620, 1971.
Kawaguchi et al., "The Journal of Antibiotics", vol. XXV, No. 12, pp. 695-708.
Courvalin et al., "Antimicrobial Agents and Chemotherapy", Apr. 1977, pp. 619-624.
Farmdoc Abstract 46482X, Bristol Myers Co., 09/12/74.
Farmdoc Abstract 41695Y, Zaidan Hojin Biseib 09/12/75.
Tsuchiya et al., "Jour. of Antibiotics", vol. XXXII, No. 12, pp. 1351-1353, 1979.

Primary Examiner—Johnnie R. Brown
Attorney, Agent, or Firm—Herbert W. Taylor, Jr.

[57] ABSTRACT

3',4'-Dideoxy derivative and 1-N-((S)-α-hydroxy-ω-aminoalkanoyl)-3',4'-dideoxy derivative of kanamycin A are now synthetized from kanamycin A and show a wider and/or higher antibacterial activity than the parent kanamycin A so that they are useful in therapeutic treatment of infections by gram-negative and gram-positive bacteria, including drug-resistant strains thereof. The production of these new derivatives may be made by preparing a protected kanamycin A derivative having its 3'- and 4'-hydroxyl groups unprotected and having its all or substantially all other functional groups protected from the initial material, kanamycin A, sulfonylating the 3'- and 4'-hydroxyl groups, removing the 3'- and 4'-sulfonyloxy groups from the resulting 3',4'-disulfonic acid ester product to give a 3'-eno-kanamycin A derivative, hydrogenating the 3'-eno-kanamycin A derivative to saturate the 3',4'-unsaturated bond and to yield a protected 3',4'-dideoxykanamycin A product, followed by removal of the remainiing protective groups, and optionally further followed by 1-N-acylation of the 1-amino group of the resulting 3',4'-dideoxykanamycin A with an (S)-α-hydroxy-ω-aminoalkanoic acid or its reactive equivalent.

6 Claims, No Drawings

3',4'-DIDEOXYKANAMYCIN A AND 1-N-(S)-α-HYDROXY-ω-AMINOALKANOYL) DERIVATIVES THEREOF

SUMMARY OF THE INVENTION

This invention relates to new and useful derivatives of kanamycin A which are valuable as antibacterial agent, and also to the production of such new kanamycin A derivatives. More particularly, this invention relates to 3',4'-dideoxykanamycin A and a 1-N-(α-hydroxy-ω-aminoalkanoyl) derivative thereof, especially 1-N-(2-hydroxy-3-aminopropionyl)-3',4'-dideoxykanamycin A and 1-N-((S)-2-hydroxy-4-aminobutyryl)-3',4'-dideoxykanamycin A which are each a new compound, as well as an acid-addition salt of these new compounds.

This invention also relates to a process for the production of 3',4'-dideoxykanamycin A and to a process for the production of the 1-N-(α-hydroxy-ω-aminoalkanoyl)-3',4'-dideoxykanamycin A. This invention further relates to the applications of these new compounds as antibacterial agent.

BACKGROUND OF THE INVENTION

1. Field of the Invention

This invention relates to novel chemicals which are useful as antibacterial agents and, more specifically, to aminoglycosides such as 3',4'-dideoxykanamycin A and derivatives thereof prepared by a selectively acylating the 1-amino function with a α-hydroxy-ω-aminoalkanoyl moiety.

2. Description of the Prior Art

Kanamycins A and B were first described by Hamao Umezawa et al. as in U.S. Pat. No. 2,931,798.

3',4'-Dideoxykanamycin B was disclosed by Hamao Umezawa et al. in U.S. Pat. No. Re. 28,647 (from U.S. Pat. No. 3,753,973) and additional processes for its preparation were given by H. Umezawa et al. in U.S. Pat. No. 4,156,078 and 4,169,939 and in pending U.S. application Ser. No. 745,016 filed Nov. 26, 1976 (and abstracted as Farmdoc 41695Y).

Hamao Umezawa et al. disclosed 3',4'-dideoxykanamycin C in U.S. Pat. No. 4,120,955.

1-N-[α-Hydroxy-ω-aminoalkanoyl] derivatives of 3',4'-dideoxykanamycin B etc. were disclosed in U.S. Pat. No. 4,001,208 and corresponding derivatives of kanamycin A and B were disclosed in U.S. Pat. Nos. 3,781,268, 3,886,139 and 3,904,597 with improved processes set forth in U.S. Pat. Nos. 472,781 and 472,780.

6'-N-Methyl-1-N-[α-hydroxy-ω-aminoalkanoyl] derivatives of 3',4'-dideoxykanamycin B were described by H. Umezawa et al. in U.S. Pat. No. 4,147,861.

1-N-[α-Hydroxy-ω-aminobutyryl]-6'-methyl derivatives of kanamycins A and B were described by Umezawa et al. in U.S. Pat. No. 4,170,642 and 4,001,208 respectively (and see also Farmdoc abstract 46482X).

Some of the present inventors, H. Umezawa et al have found that drug-resistant strains of gram-negative bacteria isolated from patients, resistant *Staphylococcus aureus* and *Pseudomonas aeruginosa* and some kinds of resistant bacteria produce an enzyme (phosphotransferase) which is capable of phosphorylating 3'-hydroxyl group of kanamycin A, kanamycin B and other analogous aminoglycosidic antibiotics, and that these aminoglycosidic antibiotics can lose their antibacterial activity by phosphorylation of the 3'-hydroxyl group through the action of the phosphorylating enzyme ("Science" Vol. 157, pages 1559–1561 (1967)). After this finding was obtained, extensive researches have been made about the mechanism of resistance of bacteria to aminoglycosidic antibiotics. At present, it is found that one or some of hydroxyl groups present in the aminoglycosidic antibiotic, such as hydroxyl groups at the 4'- and/or 2"-positions of the aminoglycoside molecule can be phosphorylated or adenylylated by a wide variety of resistant bacterial strains so that the parent aminoglycosidic antibiotic can lose the antibacterial activity. Based on this finding, we already semisynthetically prepared many semi-synthetic aminoglycosidic antibiotic derivatives which are active even against the resistant strains. Among the semi-synthetic aminoglycosidic antibiotic derivatives, 3',4'-dideoxykanamycin B (see U.S. Pat. No. 3,753,973) is known under the general name "dibekacin" and is now used widely in therapeutic treatment of bacterial infections in clinics, because dibekacin is remarkably active against a wide variety of resistant bacteria.

It was very epochal to make the discovery that the removal of 3'- and 4'-hydroxyl groups from kanamycin B, that is, the 3',4'-di-deoxygenation of kanamycin B gives a semi-synthetic substance which does not lose the antibacterial activity of the parent material kanamycin B but rather attain an improved or modified antibacterial activity even against the resistant bacteria.

On the other hand, it was known that butirosins which were aminoglycosidic antibiotics produced by a *Bacillus* species were active against some kanamycin- and ribostamycin-resistant bacteria. These butirosins have been identified as 1-N-((S)-2-hydroxy-4-aminobutyryl)-5-O-β-D-xylofuranosyl- or ribofuranosyl-neamine [see the "Tetrahedron Letters" Vol. 28, pages 2617–2620 (1971)].

From comparison of the antibacterial activity of ribostamycin with that of butirosin B, it was discovered the (S)-2-hydroxy-4-aminobutyryl substituent on 1-amino group of butirosins has an important role in making ribostamycin highly active even against the resistant bacteria. From this discovery, it was deduced that an aminoglycosidic antibiotic can be imparted with an anti-bacterial activity against the resistant bacteria by introducing an aminoacyl group into the 1-amino group of an aminoglycosidic antibiotic. After this discovery, the 1-N-aminoacylation has been applied to a variety of aminoglycosidic antibiotics. A successful application of the 1-N-aminoacylation is exemplified by amikacin (also termed as BB-K8), that is, 1-N-((S)-2-hydroxy-4-aminobutyryl)-kanamycin A (see the "Journal of Antibiotics" Vol. 25, pages 695–708 (1972); U.S. Pat. No. 3,781,268).

In spite of the presence of 3'- and 4'-hydroxyl groups in the amikacin molecule, amikacin cannot be inactivated by the kanamycin-resistant bacteria owing to that the 3'- and 4'-hydroxyl groups can neither be phosphorylated nor be adenylylated under the action of the 1-N-((S)-2-hydroxy-4-aminobutyryl) substituent of amikacin. While, as amikacin is applied much more frequently and widely in clinics, new types of the resistant bacteria which are resistant to amikacin are going to occur. In the most recent years, there have been made some reports to show that the 4'-hydroxyl group of amikacin is adenylylated by certain new strains of the resistant bacteria, and that the 3'-hydroxyl group of amikacin is phosphorylated (see the "Antimicrobial Agents and Chemotherapy" pages 619–624 (1977), for example).

In view of the above-mentioned facts and observations, we expect that if the 3'-and 4'-hydroxyl groups can be removed from kanamycin A, the 3',4'-dideoxykanamycin A so possibly obtained will be active against the new types of the resistant bacteria, too.

However, it has been confirmed experimentally that when kanamycin A is merely subjected to the method of deoxygenation comprising 3',4'-di-O-sulfonylation and subsequent treatment of the 3',4'-di-O-sulfonic acid ester with sodium iodide and zinc powder which was successfully applicable in the semi-synthesis of 3',4'-dideoxykanamycin B, there cannot yet be obtained 3',4'-dideoxykanamycin A as expected. This is because the kanamycin A molecule contains 2'-hydroxyl group adjacent to the 3'-hydroxyl group thereof so that this 2'-hydroxyl group can be sulfonylated concurrently to the sulfonylation of the 3'- and 4'-hydroxyl groups, with a consequence that the 2'-hydroxyl group once sulfonylated can be removed at the same time as when the removal of the sulfonylated 3'- and 4'-hydroxyl groups is performed by treating with sodium iodide and zinc powder.

Accordingly, we have considered that 3',4'-dideoxykanamycin A cannot be synthetized from kanamycin A by applying thereto the same deoxygenation method as the one which was adopted in the synthesis of 3',4'-dideoxykanamycin b from kanamycin B, unless we are not able to prepare and provide such a protected kanamycin A derivative which is to be subjected to the procedure of de-oxygenation as mentioned above and of which the 3'- and 4'-hydroxyl groups of kanamycin A remain in the unprotected state, while the neighboring 2'-hydroxyl groups as well as all the other hydroxyl groups and all the amino groups are existing in the protected or blocked state. However, no great difference is observed between the 2'-, 3'- and 4'-hydroxyl groups of kanamycin A in respect of their reactivity, and hence it was very difficult to find out any procedure by which the 2'-hydroxyl group can be protected with retaining the 3'- and 4'-hydroxyl groups unblocked.

We have researched extensively in an attempt to provide such suitable kanamycin A derivative. As a result, we have now found that such a protected derivative of kanamycin A having 3'- and 4'-hydroxyl groups unblocked, having a protected or unprotected 2''-hydroxyl group and having the other hydroxyl groups (including 2'-hydroxyl group) as well as all the amino groups blocked is prepared by means of a combination of an ingenious choice of the nature of the hydroxyl-protecting and amino-protecting groups employed, with an elaborate arrangement of the sequence of the respective stages of protecting each amino group and each hydroxyl groups, in such a way that the 6'-amino group of kanamycin A which is the most reactive among the four amino groups of kanamycin A is at first blocked by an alkoxycarbonyl group, an aralkyloxycarbonyl group, especially benzyloxycarbonyl group or an aryloxycarbonyl group known as one of the conventional amino-protecting groups; the 1-, 3- and 3''-amino groups of kanamycin A are then protected with a hydrocarbylsulfonyl group such as an alkylsulfonyl group, an arylsulfonyl group or aralkylsulfonyl group; the free 4'-hydroxyl group and the alkoxycarbonylated, aralkyloxycarbonylated or aryloxycarbonylated 6'-amino group are subsequently condensed with each other into the form of a cyclic carbamate by treating with e.g. sodium hydride, resulting in a simultaneous protection of the 4'-hydroxyl and 6'-amino groups; a pair of the 5-hydroxyl group and 2'-hydroxyl group are selectively and simultaneously blocked by introducing and bridging therebetween with a known divalent hydroxyl-protecting group such as an alkylidene group, specially isopropylidene group, cyclohexylidene group, benzylidene group or tetrahydro-4-pyranylidene group; the 4',6'-carbamate ring once formed is ring-fissioned by treatment with an alkali to regenerate the free 4'-hydroxyl group and the free 6'-amino group; and finally the free 6'-amino group is blocked with an alkoxycarbonyl or aralkyloxycarbonyl group or an alkanoyl group such as acetyl. In this way, we have succeeded in preparing a desired, suitable protected derivative of kanamycin A, and as a consequence of it, we have now succeeded to provide a route by which semi-synthesis of 3',4'-dideoxykanamycin A is achieved.

Thus, we have now firstly succeeded in synthetizing the new compound, 3',4'-dideoxykanamycin A, and we have also succeeded in synthetizing a 1-N-(α-hydroxy-ω-aminoalkanoyl)-3',4'-dideoxykanamycin A, particularly 1-N-(2-hydroxy-3-aminopropionyl)-3',4'-dideoxykanamycin A and 1-N-((S)-2-hydroxy-4-aminobutyryl)-3',4'-dideoxykanamycin A by condensing the 1-amino group of 3',4'-dideoxykanamycin A with an isoseryl group, particularly DL- or L- or D-2-hydroxy-3-aminopropionyl group, or with (S)-2-hydroxy-4-aminobutyryl group. We have further found that the new derivative of kanamycin A which we have now synthetized are active against a wide variety of the resistant bacteria.

DETAILED DESCRIPTION OF THE INVENTION

According to a first aspect of this invention, therefore, there are provided as a new compound 3',4'-dideoxykanamycin A and a 1-N-(α-hydroxy-ω-aminoalkanoyl) derivative of 3',4'-dideoxykanamycin A represented by the general formula:

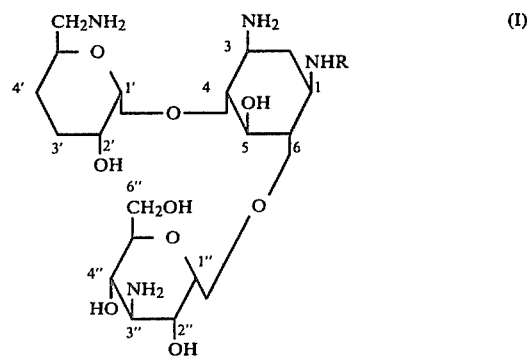

wherein R represents a hydrogen atom or an α-hydroxy-ω-aminoalkanoyl group of the formula

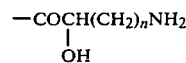

wherein n is an integer of 1 or 2; and pharmaceutically acceptable acid-addition salts thereof.

The new compound of the general formula (I) according to the first aspect of this invention includes 3',4'-dideoxykanamycin A of the formula:

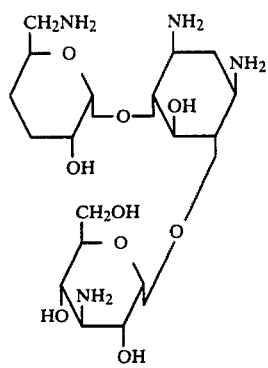

as well as 1-N-(2-hydroxy-3-aminopropionyl)-3',4'-dideoxykanamycin A and 1-N-(2-hydroxy-4-aminobutyryl)-3',4'-dideoxykanamycin A represented by a general formula:

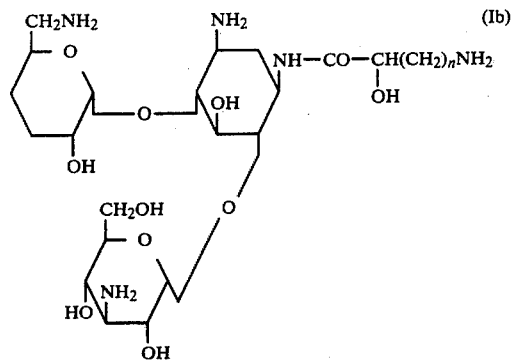

wherein n is an integer of 1 or 2.

Physico-chemical and biological properties of the particular new compounds according to this invention are described below.

3',4'-Dideoxykanamycin A is in the form of a colorless powder which does not show any definite melting point. Its carbonate gave an elemental analysis (C 44.22, H 7.34, N 10.45%) which was substantially coincident with its molecular formula ($C_{18}H_{36}N_4O_9.1.1$ $H_2CO_3$). Specific optical rotation of it was $[\alpha]_D^{25}+116°$ (c=1, water).

1-N-(DL-2-hydroxy-3-aminopropionyl)-3',4'-dideoxykanamycin A is in the form of a colorless powder which does not show a definite melting point. Specific optical rotation $[\alpha]_D^{25}+93°$ (c=1, water).

1-N-((S)-2-hydroxy-4-aminobutyryl)-3',4'-dideoxykanamycin A is also in the form of a colorless powder which does not show any definite melting point. Specific optical rotation $[\alpha]_D^{25}+91°$ (c=1, water).

The minimum inhibitory concentrations (mcg/ml) of the new compounds of this invention against various microorganisms were determined according to a standard serial dilution method using nutrient agar incubation medium at 37° C., the estimation being made after 18 hours incubation. For comparison purpose, the MIC. of kanamycin A, amikacin and dibekacin was also determined under the same test conditions. The test results so obtained are shown in Table 1 below as the antibacterial spectra of the new compounds of this invention.

TABLE 1

Antibacterial spectra of 3',4'-dideoxykanamycin A (Compound No. 1); 1-N-((S)-2-hydroxy-4-aminobutyryl)-3',4'-dideoxykanamycin A (Compound No. 2); 1-N-(DL-2-hydroxy-3-aminopropionyl)-3',4'-dideoxykanamycin A (Compound No. 3) in comparison with kanamycin A, amikacin and dibekacin.

| Test Microorganisms | Kanamycin A | Compound No. 1 | Amikacin | Compound No. 2 | Compound No. 3 | Dibekacin |
|---|---|---|---|---|---|---|
| Staphylococcus aureus 209P | 3.12 | 3.12 | 3.12 | 1.56 | 3.12 | 0.78 |
| Staphylococcus aureus APOI | 12.5 | 3.12 | 1.56 | 0.78 | 1.56 | 0.78 |
| Staphylococcus aureus MS 9610 | 6.25 | 6.25 | 3.12 | 1.56 | 3.12 | — |
| Staphylococcus aureus MS 9883 | 6.25 | 6.25 | 6.25 | 3.12 | 3.12 | — |
| Staphylococcus epidermides 109 | 25 | 6.25 | 3.12 | 0.78 | 3.12 | 0.78 |
| Sarcina lutea PCI 1001 | 12.5 | 12.5 | 3.12 | 3.12 | 6.25 | 25 |
| Klebsiella pneumoniae 22 #3038 | >100 | >100 | 3.12 | 3.12 | 3.12 | >100 |
| Escherichia coli K-12 | 3.12 | 6.25 | 1.56 | 1.56 | 1.56 | 1.56 |
| Escherichia coli K-12 ML 1629 | >100 | 6.25 | 1.56 | 1.56 | 1.56 | 1.56 |
| Pseudomonas aeruginosa A3 | 25 | 6.25 | 1.56 | 3.12 | 3.12 | 0.78 |
| Klebsiella THO | >100 | 6.25 | 6.25 | 1.56 | 1.56 | 1.56 |
| Klebsiella HOU | >100 | >100 | 12.5 | 3.12 | 3.12 | >100 |
| Klebsiella BRIA | >100 | >100 | 6.25 | 1.56 | 3.12 | >100 |
| Serratia CAT | >100 | 12.5 | 12.5 | 6.25 | 12.5 | 6.25 |
| Serratia BOT | 6.25 | 50 | 12.5 | 6.25 | 12.5 | 25 |
| Serratia 7 | >100 | >100 | 12.5 | 3.12 | 6.25 | >100 |
| Providencia 19 | >100 | 100 | 12.5 | 3.12 | 6.25 | >100 |
| Providencia ZAO | >100 | 12.5 | 12.5 | 6.25 | 12.5 | >100 |
| Providencia Pv 37 | >100 | >100 | 12.5 | 6.25 | 6.25 | >100 |
| Proteus vulgaris BAC | >100 | 3.12 | 3.12 | 1.56 | 3.12 | 12.5 |
| Proteus rettgeri AUB | >100 | >100 | 6.25 | 3.12 | 6.25 | 100 |
| Enterobacter 666 | >100 | 100 | 1.56 | 0.78 | 1.56 | >100 |
| Enterobacter HAU | >100 | 12.5 | 50 | 12.5 | 25 | >100 |
| Erwinia 7-22 | >100 | >100 | 1.56 | 0.78 | 1.56 | >100 |
| Pyocyanique | 50 | >100 | 50 | 12.5 | 50 | 6.25 |

As will be clear from the above table, 3',4'-dideoxykanamycin A exhibits a remarkably higher antibacterial activity against various resistant bacteria than the parent kanamycin A, and 1-N-((S)-2-hydroxy-4-aminobutyryl)-3',4'-dideoxykanamycin A exhibits a higher antibacterial activity against the various resistant bacteria than amikacin, i.e. 1-N-((S)-2-hydroxy-4-aminobutyryl)-kanamycin A. This property that the new compounds of this invention show an improvement in the antibacterial activity against the resistant bacteria over the known kanamycin A and amikacin may be expected to be enhanced in future, as amikacin is getting a decreased antibacterial activity against the resistant bacteria. According to the new findings of the present inventors obtained in this invention, it may perhaps be said that when an aminoglycosidic antibiotic is modified by subjecting it to the 3',4'-di-deoxygenation and to the 1-N-aminoacylation in combination, such modification will give such an aminoglycosidic antibiotic derivative which exhibits a higher antibacterial activity against the resistant bacteria than such one which might be obtained by subjecting the aminoglycosidic antibiotic either to the 3',4'-di-deoxygenation or to the 1-N-aminoacylation solely.

The acid-addition salt of the new compounds of the general formula (I) according to this invention may be the pharmaceutically acceptable one and includes, for example, a salt thereof with a pharmaceutically acceptable inorganic acid such as hydrochloric acid, hydrobromic acid, sulfuric acid, phosphoric acid, nitric acid and the like or with a pharmaceutically acceptable organic acid such as acetic acid, maleic acid, citric acid, ascorbic acid, methanesulfonic acid and the like.

The 3',4'-dideoxykanamycin A compounds of the general formula (I) according to this invention are usually obtained in the form of the free base, a hydrate or a carbonate thereof from the process of preparing them, but they may be converted into a pharmaceutically acceptable acid-addition salt by reacting with a pharmaceutically acceptable inorganic or organic acid as described above.

All of the new compounds of the general formula (I) according to this invention have a low toxicity, as demonstrated by that they all exhibit an $LD_{50}$ value of not less than 200 mg/kg upon intravenous injection in mice for estimation of their acute toxicity. Therefore, the new compounds of this invention are useful in therapeutic treatment of infections by various gram-negative and gram-positive bacteria, including the resistant bacterial strains. When estimating the acute toxicity by intravenous injection of gentamicin, dibekacin and their 1-N-acyl derivatives, some of which are being widely used clinically, it has been found that these compounds all have an $LD_{50}$ value ranging of 80–120 mg/kg. Accordingly, the low toxicity of the above new compounds of general formula (I) according to this invention is noteworthy, and the low toxicity of the new compounds of this invention with retaining the antibacterial activity substantially as high as that of the above-described known drugs will facilitate the clinical use of the new compounds, fulfilling the modern demand for providing efficient and less toxic drugs.

According to a second aspect of this invention, there is provided a process for the production of the new compound of the formula (Ia) shown hereinbefore. Thus, the second aspect of this invention provides a process for the production of 3',4'-dideoxykanamycin A which comprises the stages of:

(a) treating a protected derivative of kanamycin A of the formula:

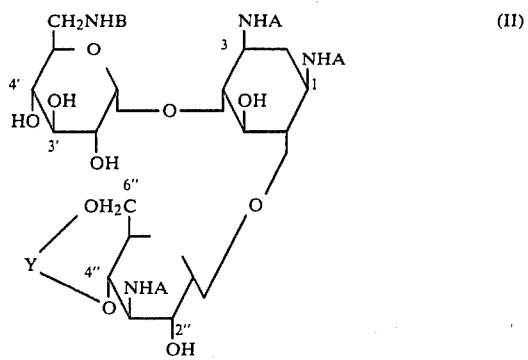

wherein each A represents an alkylsulfonyl group containing 1 to 4 carbon atoms, an arylsulfonyl group, specially tosyl or an aralkylsulfonyl group, specially benzylsulfonyl as an amino-protecting group, B represents an alkoxycarbonyl group containing 2 to 5 carbon atoms, an aralkyloxycarbonyl group, specially benzyloxycarbonyl or an aryloxycarbonyl group, and Y represents a divalent hydroxyl-protecting group, especially an alkylidene group containing 1 to 6 carbon atoms (preferably isopropylidene), cyclohexylidene, benzylidene or tetrahydro-4-pyranylidene group, with a basic reagent such as sodium hydride under anhydrous conditions in an organic solvent to produce a 4',6'-cyclic carbamate derivative of the formula:

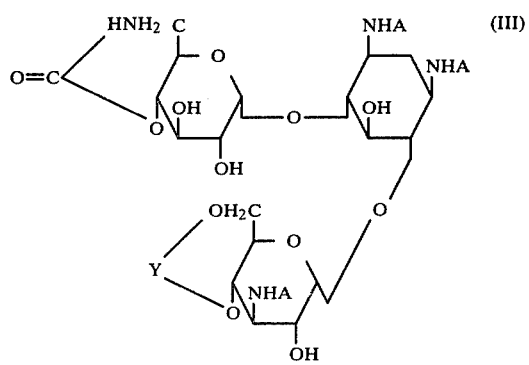

wherein A and Y are as defined above;

(b) reacting the 4',6'-carbamate compound of the formula (III) with 2,2-dimethoxypropane, 1,1-dimethoxycyclohexane, benzaldehyde, dimethylacetal or 5,6-dihydro-4-methoxy-2H-pyran under anhydrous conditions in an organic solvent in the presence of an acidic catalyst to produce a 2',5-O-protected derivative of the formula:

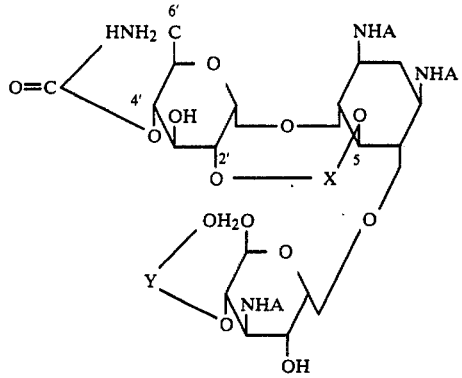

(IV)

an organic solvent to produce a 2",3',4'-tri-O-sulfonyl derivative of the formula:

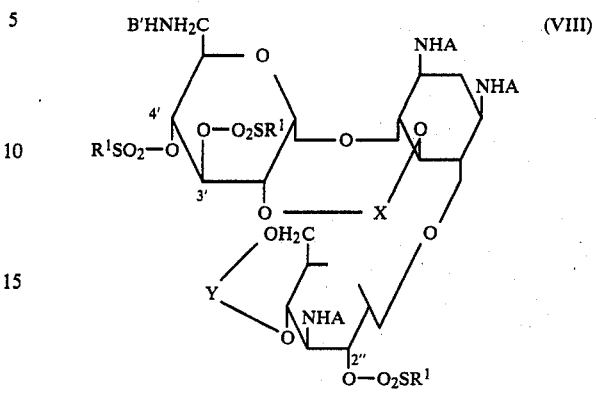

(VIII)

wherein A, B', $R^1$, X and Y are as defined above;

(e) converting the resulting 2",3'-4',tri-O-sulfonylkanamycin A compound into the 3'-eno-kanamycin A compound by treating with an alkali metal iodide in the absence of zinc metal powder;

(f) converting the 3'-eno-kanamycin A compound into the 3',4'-dideoxykanamycin A compound by reducing with hydrogen in the presence of a hydrogenation catalyst to saturate the 3',4'-unsaturated bond of the 3'-eno-kanamycin A compound;

(g) removing the hydroxyl-protecting groups (X and Y) remaining at the 5-, 2'-, 4"- and 6"-positions of the kanamycin A compound by acid hydrolysis in a known manner;

(h) removing the amino-protecting group (B') remaining at the 6'-amino group of the kanamycin A compound in a known manner;

(i) removing the 2"-O-sulfonyl group ($-O_2SR^1$) remaining at the 2"-hydroxyl group and also all the sulfonyl groups (A) remaining at the 1-, 3- and 3"-amino groups of the kanamycin A compound by treating with an alkali metal or alkaline earth metal in liquid ammonia; and each of the aforesaid stages (g), (h) and (i) being effected in any optional sequence of these stages one after another and at any time after the stage (d) of reacting the 3',4'-dihydroxy-kanamycin A compound of the formula (V) with the sulfonylating agent (VI), (VI') or (VI") having been made.

In the process of the second aspect of this invention, therefore, it is possible as an embodiment or a modification thereof to carry out the present process via such a route where (1) the aforesaid stage (d) is followed, for example, by the under-mentioned successive stages in the following sequence:

converting the resulting 2",3',4'-tri-O-sulfonylkanamycin A compound of the formula (VII) into the corresponting 3'-eno-kanamycin A compound of the formula:

wherein A and Y are as defined above and X may be the same as or different from Y and represents isopropylidene, cyclohexylidene, benzylidene or tetrahydro-4-pyranylidene group; followed by isolating the 2',5-O-protected derivative (IV) from the by-produced 2',3'-O-protected derivative;

(c) hydrolizing the 2',5-O-protected compound of the formula (IV) under alkaline conditions to fission the 4',6'-carbamate ring and to regenerate the free 4'-hydroxyl group and free 6'-amino group, followed by alkoxycarbonylating, aralkyloxycarbonylating or alkanoylating (especially acetylating) the free 6'-amino group of the ring-fission product to give a 3',4'-dihydroxy derivative of the formula:

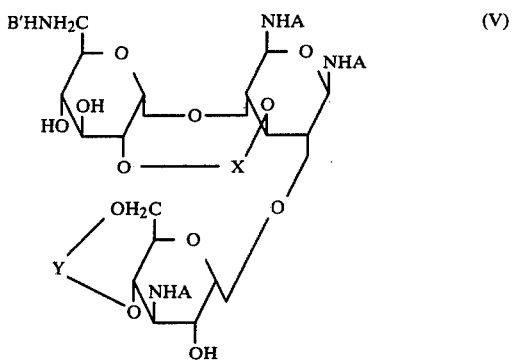

(V)

wherein A, Y and X are as defined above and B' represents an alkoxycarbonyl group containing 2 to 5 carbon atoms, an aralkyloxycarbonyl group, specially benzyloxycarbonyl or an alkanoyl group, specially acetyl;

(d) sulfonylating the 3',4'-dihydroxy compound of the formula (V) by reacting with an alkylsulfonyl or aralkylsulfonyl chloride or bromide of the formula:

 (VI)

or

 (VI')

or a corresponding sulfonic acid anhydride of the formula:

 (VI")

wherein $R^1$ represents an alkyl group containing 1 to 4 carbon atoms or an aralkyl group, especially benzyl, as the sulfonylating agent under anhydrous conditions in

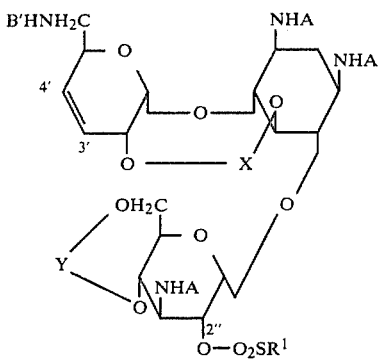

by treating the compound (VII) with an alkali metal iodide in the absence of zinc metal powder;

removing the hydroxyl-protecting groups (X and Y) remaining at the 5-, 2'-, 4"- and 6"-positions of the 3'-eno-kanamycin A compound (VIII) by acid hydrolysis in a known manner;

converting the 3'-eno-kanamycin A compound so partially deprotected into the corresponding 3',4'-dideoxykanamycin A compound by reducing with hydrogen in the presence of a hydrogenation catalyst to saturate the 3',4'-unsaturated bond of the 3'-eno-kanamycin A compound;

removing the amino-protecting group (B') remaining at the 6'-amino group (B') of the 3',4'-dideoxykanamycin A compound obtained as the hydrogenation product in the just preceding state; and removing from the 3',4'-dideoxykanamycin A compound so partially further deprotected the residual 2"-O-sulfonyl group (—O₂SR¹) remaining at the 2'-hydroxyl group and also all the sulfonyl groups (A) remaining at the 1-, 3- and 3"-amino groups of the 3',4'-dideoxykanamycin A compound by treating the latter with an alkali metal or alkaline earth metal in liquid ammonia, whereby the desired 3',4'-dideoxykanamycin A is afforded:

or alternatively (2) the aforesaid stage (d) is followed by the under-mentioned subsequent stages in the following order:

converting the resulting 2",3',4'-tri-O-sulfonylkanamycin A compound of the formula (VII) into the corresponding 3'-eno-kanamycin A compound of the formula (VIII) by treating the compound (VII) with an alkali metal iodide in the absence of zinc metal powder;

converting the 3'-eno-kanamycin A compound (VIII) into the corresponding 3',4'-dideoxykanamycin A compound by reducing with hydrogen in the presence of a hydrogenation catalyst to saturate the 3',4'-unsaturated bond of the 3'-eno-kanamycin A compound;

removing the amino-protecting group (B') remaining at the 6'-amino group of the 3',4'-dideoxykanamycin A compound so obtained in a known manner;

removing from the 3',4'-dideoxykanamycin A compound so partially deprotected the hydroxyl-protecting groups (X and Y) remaining at the 5-, 2'-, 4"- and 6"-positions of the 3',4'-dideoxykanamycin A compound by acid hydrolysis in a known manner; and removing from the 3',4'-dideoxykanamycin A compound so partially further deprotected the residual 2"-O-sulfonyl group (—O₂SR¹) remaining at the 2"-hydroxyl group and also all the sulfonyl groups (A) remaining at the 1-, 3- and 3"-amino groups of the 3',4'-dideoxykanamycin A compound by treating the latter with an alkali metal or alkaline earth metal in liquid ammonia, whereby the desired 3',4'-dideoxykanamycin A is afforded:

or further alternatively (3) the aforesaid stage (d) is followed by the under-mentioned later stages in the following succession:

converting the resulting 2",3',4'-tri-O-sulfonylkanamycin A compound of the formula (VII) into the corresponding 3'-eno-kanamycin A compound of the formula (VIII) by treating the compound (VII) with an alkali metal iodide in the absence of zinc metal powder;

removing from the 3'-eno-kanamycin A compound (VIII) the hydroxyl-protecting groups (X and Y) remaining at the 5-, 2'-, 4"- and 6"-positions of the 3'-eno-kanamycin A compound by acid hydrolysis in a known manner;

removing from the 3'-eno-kanamycin A compound so partially deprotected the residual amino-protecting group remaining at the 6'-amino group of the 3'-eno-kanamycin A compound in a known manner;

removing from the 3'-eno-kanamycin A compound so partially further deprotected the residual 2"-O-sulfonyl group (—O₂SR¹) remaining at the 2"-hydroxyl group and also all the sulfonyl groups (A) remaining at the 1-, 3- and 3"-amino groups of the 3'-eno-kanamycin A compound by treating the latter with an alkali metal or alkaline earth metal in liquid ammonia; and converting the 3'-eno-kanamycin A compound so entirely deprotected into 3',4'-dideoxykanamycin A by reducing with hydrogen in the presence of a hydrogenation catalyst to saturate the 3',4'-unsaturated bond of the 3'-eno-kanamycin A compound, whereby the desired 3',4'-dideoxykanamycin A is obtained.

In the process of the second aspect invention, the stage (d) of reacting the 3',4'-dihydroxy compound (V) with an alkylsulfonyl or aralkylsulfonyl halide (VI) or (VI') or a corresponding sulfonic acid anhydride (VI") involves the sulfonylation of the 2"-hydroxyl group of the compound (V), and the stage (e) of reacting the resulting 2",3'-4'-tri-O-sulfonyl compound (VII) with an alkali metal iodie for the purpose of the 3'-enoation must be effected in the absence of zinc metal powder. If the presence of zinc metal powder would be provided in this stage (e), the formation of an aziridine ring between the 3"-amino group and the 2"-sulfonyloxy group should be accompanied, giving an undesired derivative. Therefore, it is preferred to protect previously the 2"-hydroxyl group of the 3',4'-dihydroxy compound (V) with an appropriate hydroxyl-protecting group, before the compound (V) is reacted with the sulfonylation agent of the formula (VI), (VI') or (VI"). The process of the second aspect invention may be further modified so that a stage of protecting the 2"-hydroxyl group of the compound (V) is interposed therein.

According to a third aspect of the invention, therefore, there is provided, as a modification of the process of the second aspect invention, a process for the production of 3',4'-dideoxykanamycin A, which comprises the stages of:

(a) treating a protected derivative of kanamycin A of the formula (II) shown hereinbefore, with a basic reagent such as sodium hydride under anhydrous conditions in an organic solvent to produce the 4',6'-cyclic carbamate derivative of the formula (III) shown hereinbefore;

(b) reacting the 4',6'-carbamate compound of the formula (III) shown hereinbefore, with 2,2-dimethoxypropane, 1,1-dimethoxycyclohexane, benzaldehyde, dimethylacetal or 5,6-dihydro-4-methoxy-2H-pyran under anhydrous conditions in an organic solvent in the presence of an acidic catalyst to produce the 2',5-O-protected derivative of the formula (IV) shown hereinbefore, followed by isolating the 2',5-O-protected derivative (IV) from the by-produced 2',3'-O-protected derivative;

(j) protecting the 2"-hydroxyl group of the 2',5-O-protected compound of the formula (IV) by (1) reacting this 2',5-O-protected compound (IV) with acetyl chloride or acetyl anhydride in pyridine to produce a 3',2"-di-O-acetylated derivative of the formula:

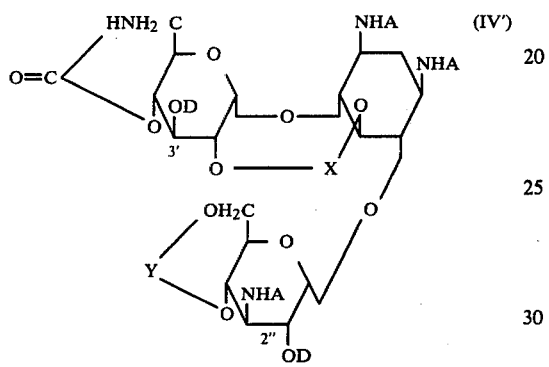

wherein A, X and Y are as defined hereinbefore and each D represents an acetyl group, (2) subsequently treating the 3',2"-di-O-acetylated derivative (IV') with an ammoniacal alkanol, particularly ammoniacal ethanol to remove preferentially the 2"-acetyl group therefrom and to give the corresponding 3'-mono-O-acetylated derivative, and (3) reacting said 3'-mono-O-acetylated derivative with 3,4-dihydro-2H-pyran under anhydrous conditions in an organic solvent to convert the 2"-hydroxyl group into 2"-tetrahydropyranyloxy group;

(c') hydrolyzing the resulting 2"-tetrahydropyranyloxy-4',6'-carbamate product under alkaline conditions to remove the 3'-O-acetyl group therefrom and to fission the 4',6'-carbamate ring, giving a 2"-O-protected ring-fission derivative of the formula

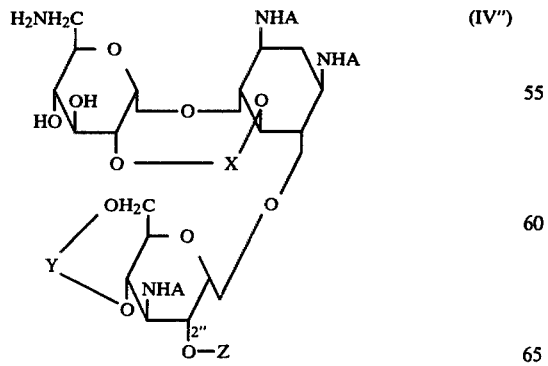

wherein A, X and Y are as defined above and Z represents tetrahydropyranyl group

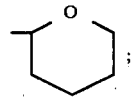

followed by alkoxycarbonylating, aralkyloxycarbonylating or alkanoylating the free 6'-amino group of the 2"-O-protected ring-fission product of the formula (IV"') to give a 3',4'-dihydroxy-2"-O-protected derivative of the formula:

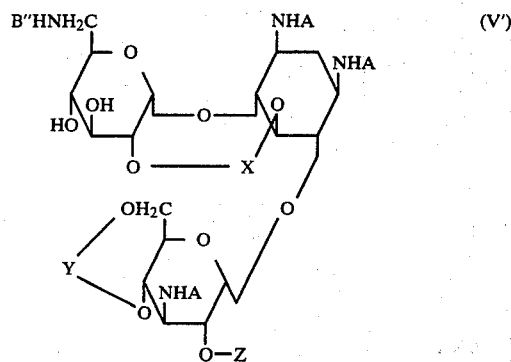

wherein X, Y and Z are as defined above and B" represents an alkoxycarbonyl group containing 2 to 5 carbon atoms, an aralkyloxycarbonyl group, specially benzyloxycarbonyl or an alkanoyl group, specially acetyl;

(d') sulfonylating the 3',4'-dihydroxy-2"-O-protected derivative of the formula (V') by reacting with an alkylsulfonyl or aralkylsulfonyl chloride or bromide of the aforesaid formula (VI) of (VI') or a sulfonic acid anhydride of the aforesaid formula (VI") under anhydrous conditions in an organic solvent, particularly in pyridine to produce a 3',4'-di-O-sulfonyl derivative of the formula:

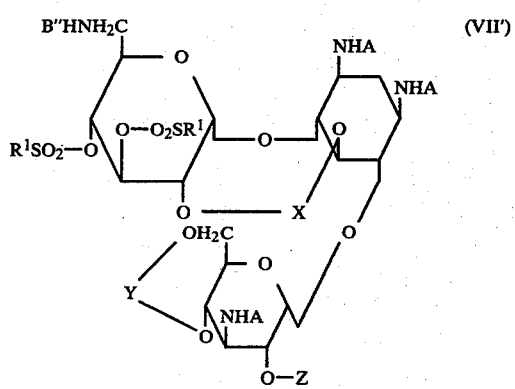

wherein A, B", $R^1$, X, Y and Z are as defined above:

(e') converting the resulting 3',4'-di-O-sulfonylkanamycin A compound into the 3'-eno-kanamycin A compound by treating with an alkali metal iodide in the presence of zinc metal powder or with sodium iodide alone;

(f') converting the 3'-eno-kanamycin A compound into the 3',4'-dideoxykanamycin A compound by reducing with hydrogen in the presence of a hydrogenation catalyst to saturate the 3',4'-unsaturated bond of the 3'-eno-kanamycin A compound;

(g') removing the hydroxyl-protecting groups (X, Y and Z) remaining at the 5-, 2'-, 4"- and 6"- as well as 2"-positions of the kanamycin A compound by acid hydrolysis;

(h') removing the amino-protecting group (B") remaining at the 6'-amino group of the kanmycin A compound in a known manner;

(i') removing all the sulfonyl groups (A) remaining at the 1-, 3- and 3"-amino groups of the kanamycin A compound by treating with an alkali metal or alkaline earth metal in liquid ammonia; and each of the aforesaid stages (g'), (h') and (i') being effected in any optional sequence of these stages one after another and at any time after the stage (d') of sulfonylating the 3',4'-dihydroxy-kanamycin A compound of the formula (V') with the sulfonylating agent (VI), (VI') or (VI") having been made.

In the presence of the third aspect of this invention, it is also possible as an embodiment or a modification thereof to carry out the present process via such a route where (1) the aforesaid stage (d') is followed, for example, by the under-mentioned successive stages in the following sequence:

removing the hydroxyl-protecting groups (X, Y and Z) remaining at the 5-, 2'-, 4"- and 6"- as well as 2"-positions of the 3',4'-di-O-sulfonyl-kanamycin A compound of the formula (VII') by acid hydrolysis in a known manner;

converting the resulting partially deprotected 3',4'-di-O-sulfonyl-kanamycin A compound (namely, the 6'-N-alkyloxycarbonyl- or 6'-N-aralkyloxycarbonyl-1,3,3"-tri-N-sulfonyl-3',4'-di-O-sulfonyl-kanamycin A) into the corresponding 3'-eno-kanamycin A compound by treating with an alkali metal iodide in the presence of zinc metal powder or with sodium iodide alone;

converting the resulting 3'-eno-kanamycin A compound into the corresponding 3',4'-dideoxykanamycin A compound by reducing with hydrogen in the presence of a hydrogenation catalyst to saturate the 3',4'-unsaturated bond of the 3'-eno-kanamycin A compound;

removing the amino-protecting group (B") remaining at the 6'-amino group of the 3',4'-dideoxykanamycin A compound obtained as the hydrogenation product of the preceding stage in a known manner; and removing from the 3',4'-dideoxykanamycin A compound so partially further deprotected (namely, the 1,3,3"-tri-N-sulfonyl-3',4'-dideoxykanamycin A) all the sulfonyl groups (A) remaining at the 1-, 3- and 3"-amino groups of the 3',4'-dideoxykanamycin A compound, whereby the desired 3',4'-dideoxykanamycin A is afforded:

or alternatively (2) the aforesaid stage (d') is followed by the under-mentioned subsequent stages in the following order:

converting the resulting 3',4'-di-O-sulfonylkanamycin A compound of the formula (VII') into the corresponding 3'-eno-kanamycin A compound of the formula:

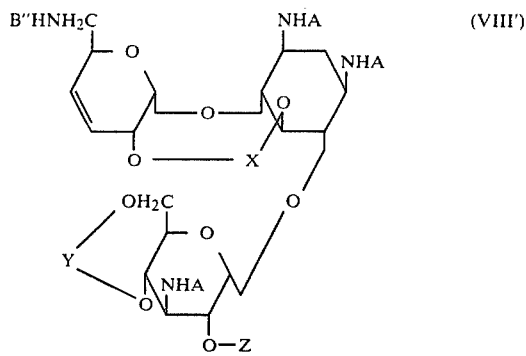

by treating the compound (VII') with an alkali metal iodide in the presence of zinc metal powder or with sodium iodide alone;

converting the 3'-eno-kanamycin A compound into the corresponding 3',4'-dideoxykanamycin A compound by reducing with hydrogen in the presence of a hydrogenation catalyst to saturate the 3',4'-unsaturated bond of the 3'-eno-kanamycin A compound;

removing from the 3',4'-dideoxykanamycin A compound obtained the residual amino-protecting group (B") remaining at the 6'-amino group of the 3',4'-dideoxykanamycin A compound in a known manner;

removing from the 3',4'-dideoxykanamycin A compound so partially deprotected the hydroxyl-protecting groups (X, Y and Z) remaining at the 5-, 2'-, 4"- and 5"- as well as 2"-positions of the 3',4'-dideoxykanamycin A compound by acid hydrolysis in a known manner; and removing from the 3',4'-dideoxykanamycin A compound so partially further deprotected all the sulfonyl groups (A) remaining at the 1-, 3- and 3"-amino groups thereof, whereby the desired 3',4'-dideoxykanamycin A is obtained: or further alternatively (3) the aforesaid stage (d') is followed by the under-mentioned stages in the following succession:

converting the resulting 3',4'-di-O-sulfonylkanamycin A compound of the formula (VII') into the corresponding 3'-eno-kanamycin A compound of the formula (VIII') by the treatment with an alkali metal iodide in the presence of zinc metal powder or with sodium iodide alone;

removing from the 3'-eno-kanamycin A compound the residual amino-protecting group (B") at the 6'-amino group thereof in a known manner;

removing from the 3'-eno-kanamycin A compound so partially deprotected the hydroxyl-protecting groups (X, Y and Z) remaining at the 5-, 2'-, 4"- and 6"- as well as 2"-positions thereof by acid hydrolysis in a known manner;

removing from the 3'-eno-kanamycin A compound so partially further deprotected all the sulfonyl groups (A) remaining at the 1-, 3- and 3"-amino groups of the 3'-eno-kanamycin A compound by treating the latter with an alkali metal or alkaline earth metal in liquid ammonia; and converting the 3'-eno-kanamycin A compound so entirely deprotected into 3',4'-dideoxykanamycin A by reducing with hydrogen in the presence of a hydrogenation catalyst to saturate the 3',4'-unsaturated bond of the 3'-eno-kanamycin A compound, whereby the desired 3',4'-dideoxykanamycin A is afforded.

The process of the second aspect of this invention is now described in detail.

Firstly, the preparation of the protected derivative of kanamycin A of the formula (II) employed as the starting material in this process may be conducted by the following procedure. Kanamycin A is used as the initial material and its 6'-amino group is protected by alkoxycarbonylating, aryloxycarbonylating or aralkyloxycarbonylating this amino group selectively in a known manner to introduce the amino-protecting alkoxycarbonyl, aryloxycarbonyl or aralkyloxycarbonyl group (B). As the 6'-amino group is much reactive than the other amino groups of kanamycin A, the amino-protecting group (B) of an alkoxycarbonyl, aryloxycarbonyl or aralkyloxycarbonyl type may be introduced preferentially into the 6'-amino group, for example, by reacting 1 molar proportion of kanamycin A (free base) in water with 0.5 to 3 molar proportion of a chloroformate of the formula:

BCl wherein B represents an alkoxycarbonyl group of 2 to 6 carbon atoms, an aryloxycarbonyl group such as phenyloxycarbonyl or an aralkyloxycarbonyl group such as benzyloxycarbonyl, at a temperature of 0° to 10° C. according to the method of Kawaguchi et al as described in the "Journal of Antibiotics" 25, 695–708 (1972) or U.S. Pat. No. 3,781,268, for example. It is then convenient to prepare, for example, 6'-N-benzyloxycarbonylkanamycin A according to the method of Example 1 of U.S. Pat. No. 3,925,353. The 6'-N-alkoxycarbonyl-, 6'-N-aryloxycarbonyl- or 6'-N-aralkyloxycarbonyl-kanamycin A so prepared may be converted into the corresponding 1,3,3''-tri-N-sulfonyl-kanamycin A by alkylsulfonylating, arylsulfonylating or aralkylsulfonylating it in an organic solvent such as aqueous dioxane.

The preparation of the 1,3,3''-tri-N-sulfonyl-kanamycin A derivative may preferably be conducted, e.g., in the following way. The 6'-N-protected kanamycin A is reacted with a substantially stoichiometric quantity (i.e. 3 molar proportion or more) of a sulfonic chloride of the formula:

R²SO₂Cl wherein R²SO₂— has the same meaning as that of the aforesaid group A, such as tosyl chloride in an inert organic solvent such as dioxane or aqueous dioxane at a temperature of 30° to 50° C. in the presence of an amount of alkali such as sodium carbonate to give the 6'-N-protected-1,3,3''-tri-N-sulfonyl-kanamycin A. The 1,3,3''-tri-N-sulfonylated kanamycin A so obtained is then reacted with an alkylidenylating agent, an aralkylidenylating agent, a cyclohexylidenylating agent such as 1,1-dimethoxycyclohexane or a tetrahydro-4-pyranylidenylating agent at a temperature of e.g. 10° to 80° C. to protect the 4''- and 6''-hydroxyl group with a divalent hydroxyl-protecting group (Y) in a known manner as described in U.S. Pat. No. 3,929,762. As the alkylidenylating agent, aralkylidenylating agent, cyclohexylidenylating agent and tetrahydro-4-pyranylidenylating agent for this purpose, there may be used such those mentioned in the U.S. Pat. No. 3,929,762. In this way, the 4''- and 6''-hydroxyl groups are protected by being converted into the form of an acetal or a ketal, giving the protected derivative of kanamycin A of the aforesaid formula (II) of which the 4''- and 6''-hydroxyl groups have been blocked simultaneously by an alkylidene group, an aralkylidene group, a cyclohexylidene group or a tetrahydro-4-pyranylidene group (Y).

In the process of the second aspect of this invention, the stage (a) thereof is conducted as follows. Thus, the protected kanamycin A derivative of the formula (II) as the starting material is dissolved in an appropriate inert organic solvent such as dimethylformamide and then reacted with a basic reagent, particularly an alkali metal hydride such as sodium hydride similarly to a known method as described in the "Journal of Antibiotics" Vol. 25, No. 12, 741–742 (1972) or U.S. Pat. No. 3,925,354 or 4,125,706 to give the 4',6'-cyclic carbamate compound of the aforesaid formula (III). If the stage (a) of forming the 4',6'-cyclic carbamate (III) is omitted in the present process and then if the starting material (II) is immediately reacted with 2,2-dimethoxypropane, 1,1-dimethoxycyclohexane, benzaldehyde or other reagents as employed in the stage (b) of the present process, the 2'-hydroxy group of the kanamycin A compound cannot be blocked selectively. Accordingly, the present process is devised to take a course in which the 4',6'-cyclic carbamate is once formed in the stage (a) and then the 2'- and 5-hydroxyl groups are blocked in the stage (b), followed by the ring-fission of the 4',6'-carbamate ring in the stage (c) to liberate the free 4'-hydroxyl group.

In the stage (b) of the present process, the 4',6'-cyclic carbamate of the formula (III) dissolved in a suitable inert organic solvent such as dichloroethane is reacted with 2,2-dimethoxypropane, 1,1-dimethoxycyclohexane, benzaldehyde or dimethylacetal or 5,6-dihydro-4-methoxy-2H-pyran under anhydrous conditions in the presence of an acidic catalyst such as toluenesulfonic acid or sulfuric acid to protect the 5- and 2'-hydroxyl groups of the kanamycin A compound with a divalent hydroxyl-protecting group derived from the acetal- or ketal-forming reagent employed. In this reaction, there are formed the 5,2'-O-protected derivative of the formula (IV) and a corresponding 2',3-O-protected derivative in substantially equal amounts. The former compound (IV) may be separated from the latter by utilizing the difference in their solubility in a proper organic solvent such as chloroform. For this purpose, a chromatographic separation is also possible.

In the stage (c) of the present process, the 2',5-O-protected compound of the formula (IV) is subjected to hydrolysis under alkaline conditions in an aqueous organic solvent such as aqueous dioxane containing an amount of an alkali metal carbonate such as sodium carbonate or barium hydroxide to fission the 4',6'-carbamate ring of the compound (IV). The hydrolysis may be effected at a temperature of 20° to 100° C. (see U.S. Pat. No. 4,125,706). As the consequence of the hydrolytic fission of the 4',6'-carbamate ring, the free 4'-hydroxyl group and free 6'-amino group are liberated. Subsequently the free 6'-amino group of the ring-fission product is blocked by alkoxycarbonylation, aralkyloxycarbonylation or alkanoylation, especially acetylation in a known manner for the purpose of second introduction of the amino-protecting group (B'). The alkoxycarbonylation or aralkyloxycarbonylation of the 6'-amino group of the ring-fission product in this stage may be conducted in a similar way to the alkoxycarbonylation or aralkyloxycarbonylation of the 6'-amino group which was effected in the procedure of preparing the protected derivative of kanamycin A of the formula (II) as described hereinbefore, and using a chloroformate of the formula:

B'Cl wherein B' represents an alkoxycarbonyl or aralkyloxycarbonyl group which may be the same as or different from the aforesaid amino-protecting alkoxycarbonyl or aralkyloxycarbonyl group (B). In this stage, however, the 6'-amino group may be protected also by alkanoylation, preferably by acetylation. The alkanoylation of the 6'-amino group may be effected in this stage using an alkanoic acid of 2 to 6 carbon atoms, such as acetic acid or an reactive equivalent thereof such as alkanoic acid chloride or anhydride. In this way, the stage (c) of the present process gives the 3',4'-dihydroxy derivative of the formula (V) in which the 3'-, 4'- and 2"-hydroxyl groups remain unprotected but all ot the other functional hydroxyl and amino groups are protected.

Subsequently to the stage (c) of the process of the second aspect invention, the stage (d) is conducted in which the 3',4'-dihydroxy derivative (V) is alkylsulfonylated or aralkylsulfonylated in an inert organic solvent, preferably in pyridine, by reacting with the sulfonylating agent (VI), (VI') or (VI") to give the 3',4',2"-tri-O-sulfonyl derivative of the formula (VII). The alkylsulfonylating agent of the formula (VI), (VI') or (VI") may suitably be a lower alkylsulfonic halide of 1–4 carbon atoms such as methanesulfonyl chloride or ethanesulfonyl chloride. The aralkylsulfonylating agent of the formula (VI) to (VI") may suitably be benzylsulfonic halide. The sulfonylation of the 3'-, 4'- and 2"-hydroxyl groups in this stage may be effected at a temperature of $-10°$ to $100°$ C. and most preferably at ambient temperature and for a reaction time of 30 minutes to 1 day.

In the stage (e) of the present process, the 2",3',4'-tri-O-sulfonyl-kanamycin A compound (VII) obtained in the above stage (d) is dissolved in an inert organic solvent and then reacted with an alkali metal iodide such as sodium iodide to be converted into the corresponding 3'-eno-kanamycin A compound. The organic solvent employed may be any inert one, if this can dissolve therein both of the tri-O-sulfonylated kanamycin A compound (VII) and the alkali metal iodide such as lithium iodide, sodium iodide and potassium iodide. Dimethylformamide, dimethysulfoxide, acetone, dioxane and the like may be suitable for this solvent. The reaction may properly be effected at a reaction temperature of $50°$ to $150°$ C. and for a reaction time of 10 minutes to 1 day. In most cases, the reaction can be completed in approximately 10 hours. By this reaction, the 3'- and 4'-sulfonyloxy groups are removed with formation of the olefinic double bond between 3'- and 4'-carbon atoms, giving the 3'-eno-kanamycin A compound. In the present process, the 3'-enoation stage (e) is effected by reacting with an alkali metal iodide in the absence of zinc metal powder. In this stage (e), zinc metal powder must not be used. If the 2",3',4'-tri-O-sulfonyl-kanamycin A compound is reacted with an alkali metal iodide in the presence of zinc metal powder, the 2"-sulfonyloxy group can react with the 3"-amino group with undesired formation of an aziridine ring, giving an undesirably modified kanamycin A derivative. In contrast, an alkali metal iodide together with zinc metal powder can be employed for the 3'-enoation if the 3',4'-O-sulfonylated kanamycin A compound has its 2"-hydroxyl group protected by any protective group other than the sulfonyl group, as this is observed in the stage (e') of the process according to the third aspect of this invention.

In the stage (f) of the present process, the 3'-eno-kanamycin A compound so obtained is converted into the corresponding 3',4'-dideoxykanamycin A compound by reducing with hydrogen in the presence of a known hydrogenation catalyst to effect the hydrogenation of the 3',4'-unsaturated bond into the saturated bond. The reduction of the 3',4'-double bond with hydrogen may be effected in a known manner eg. as described in U.S. Pat. No. 3,753,973 by passing hydrogen gas into a solution of the 3'-eno-kanamycin A compound dissolved in an inert solvent such as water, methanol, ethanol, isopropanol, acetone, dioxane, pyridine, tetrahydrofuran, dimethylformamide, cyclohexane, ethyl acetate or a mixed solvent of two or more of these liquids in the presence of a known hydrogenation catalyst such as Raney nickel, platinum, platinum oxide, palladium, palladium-on-carbon, cobalt-rhodium complex, copper and iron etc. The hydrogenation of the 3',4'-double bond may be conducted at a temperature of $-40°$ C. to $120°$ C. but preferably at a temperature of from ambient temperature to $100°$ C. and may readily proceed under a atmospheric pressure but even under an elevated pressure of 5 to 100 kg/cm$^2$. The reaction time for the hydrogenation may suitably be 0.5 to 48 hours.

The process of the second aspect invention includes also the stage (g) of removing the residual hydroxyl-protecting groups (X and Y), the stage (h) of removing the residual amino-protecting group (B') remaining at the 6'-amino group, and the stage (i) of removing the 2"-O-sulfonyl group and also all the sulfonyl groups (A) remaining at the 1-, 3- and 3"-amino groups of the kanamycin A compound. The removal of these residual protecting groups may be achieved by a known deprotecting technique normally employed in the synthesis of amides. Each of these deprotecting stages (g), (h) and (i) may be performed at an appropriate time after the stage (d) of producing the 3',4'-O-sulfonylated kanamycin A compound (VII) was conducted. The sequence in which each of the deprotecting stages (g), (h) and (i) is performed one after another may be chosen properly and optionally. For instance, the stage (g) of removing the divalent hydroxyl-protecting groups (X and Y) from the 5- and 2'-hydroxyl groups as well as from 4"- and 6"-hydroxyl groups of the kanaymcin A compound may precede the stage (f) of converting the 3'-eno-kanamycin A compound into the corresponding 3',4'-dideoxykanamycin A compound by the catalytic hydrogenation.

However, the step (i) of removing the residual 2"-O-sulfonyl group ($-O_2SR^1$) and the residual amino-protecting sulfonyl groups (A) must not be conducted just after the sulfonylation stage (d), as it could remove even the 3'- and 4'-O-sulfonyl groups just introduced. The removal of the divalent hydroxyl-protecting groups (X and Y) in the stage (g) may be performed by hydrolysis under weakly acidic conditions in the presence of acetic acid or diluted hydrochloric acid. The removal of the amino-protecting acyl group (B') from the 6'-amino group in the stage (h) may be effected by hydrogenolysis or by alkaline hydrolysis, depending on the nature of the amino-protecting group employed. When the amino-protecting group (B') is an aralkyloxycarbonyl group such as benzyloxycarbonyl, this can be removed by hydrogenolysis concurrently to the catalytic hydrogenation of the 3',4'-unsaturated bond of the 3'-eno-kanamycin A compound which is effected in the above stage (f). The removal in the stage (i) of the residual amino-protecting sulfonyl groups (A) and the residual sulfonyl group (—O$_2$SR$^1$) remaining at the 2''-hydroxyl group of the kanamycin A compound may conveniently be performed by treating with an alkali metal, specially metallic sodium or an alkaline earth metal in liquid ammonia in a way similar to the desulfonylation method as described in U.S. Pat. No. 4,169,939. Thus, when the residual amino-protecting sulfonyl groups (A) and the residual 2''-O-sulfonyl group are to be removed by the treatment with alkali metal or alkaline earth metal in liquid ammonia, this removal stage (i) may be effected by reacting with one or more of the alkali metals selected from lithium, sodium and potassium as well as the alkaline earth metals selected from calcium, magnesium and barium, in liquid ammonia at a reaction temperature of −80° C. to 0° C. and suitably for a time of 0.5 to 24 hours. The quantity of the alkali or alkaline earth metal used for this reaction may suitably be 10 to 100 mol. per mol. of the kanamycin A compound to be deprotected and may also be added at once or in small portions into the reaction mixture. After the reaction of removing the residual 2''-O-sulfonyl group and the residual amino-protecting sulfonyl groups (A) was completed, the reaction mixture may be admixed with an amount of water, an alkanol or ammonium chloride to consume up the remaining excessive quantity of the alkali metal or alkaline earth metal, followed by evaporating off the solvent (the liquid ammonia), dissolving the residual solid product in water and subjecting the resulting solution to a purification step, for example, a chromatographic process for purification purpose.

As stated hereinbefore, the sequence in which any one of the deportecting stages (g), (h) and (i) is performed one after another may be chosen properly, and hence it is to be noticed that the process of the second aspect invention may be carried out via any of the various routes (1), (2) and (3) mentioned hereinbefore. For instance, it is possible for the present process to be carried out in such a way that one or all of the deprotecting stages precedes or precede the stage of converting the 3'-eno-kanamycin A compound into the 3',4'-dideoxykanamycin A compound by the catalytic hydrogenation of the 3',4'-double bond of said 3'-eno compound, as be different from the sequence of the above descriptions of each stages of the present process given in the above. Accordingly, it is also possible in the present process that the stage (e) of converting the tri-O-sulfonylated kanamycin A compound into the 3'-eno-kanamycin A compound is followed immediately by the stage (g) of removing both of the 5,2'-O-protecting group (X) and the 4'',6''-O-protecting group (Y), for example.

The process according to the third aspect of this invention is now described.

In the process of the third aspect invention, the stages (a) and (b) thereof are entirely the same as the stages (a) and (b) of the process of the second aspect invention, respectively. Subsequently to these stages (a) and (b), there is interposed the stage (j) of protecting preferentially the 2''-hydroxyl group so as to prevent it from being sulfonylated, unlike to the stage (d) of the process of the second aspect invention. This stage (j) is comprising the three steps, that is, the step (1) of reacting the 2',5-O-protected kanamycin A compound. (IV) with acetyl chloride or anhydride in pyridine for acetylation of both the 2''- and 3'-hydroxyl groups; the step (2) of treating the resulting 3',2''-di-O-acetylated product (IV') with ammonical alkanol of 1–4 carbon atoms for the preferential removal of the 2''-O-acetyl group therefrom; and the step (3) of reacting the resulting 3'-mono-O-acetylated product with 3,4-dihydro-2H-pyran to block the 2''-hydroxyl group with a hydroxyl-protecting group, tetrahydropyranyl group which is readily removable concurrently to the removal of the divalent hydroxyl-protecting groups (X and Y) having been introduced into the 5-, 2'-, 4''- and 6''-hydroxyl group of the kanamycin A compound. The above step (1) may be performed by reacting 1 molar proportion of the 2',5-O-protected kanamycin A derivative (IV) with substantially 2 molar proportions or more of acetyl chloride or acetyl anhydride in pyridine at a temperature of 0° C. to 50° C., followed by recovering the resulting 3',2''-O-acetylated product (IV') from the reaction mixture by distilling off the pyridine therefrom. The above step (2) may be conducted by dissolving the resulting 3',2''-di-O-acetylated product (IV') in an alkanol such as methanol, ethanol or butanol containing 2 to 10N of ammonia and following the solution at a temperature of −10° C. to +50° C. for a time of 10 to 400 minutes. The step (3) may be carried out by dissolving the resulting 3'-mono-O-acetylated product in a dry organic solvent such as dichloromethane, tetrahydrofurane and admixing the resulting solution with 1 molar or more proportion of 3,4-dihydroxy-2H-pyran at ambient temperature in the presence of acidic catalyst such as p-toluenesulfonic acid.

After the 2''-O-protecting stage (j) was conducted, the resulting 2''-O-tetrahydropyranyl-kanamycin A compound (in the form of the 4',6'-carbamate) is hydrolyzed in the stage (c') of the present process in the same way as in the stage (c) of the process of the second aspect invention, when the 3'-O-acetyl group is removed therefrom and simultaneously the fussion of the 4',6'-cyclic carbamate takes place so that the 3'- and 4'-hydroxyl groups as well as the 6'-amino group are liberated in the free state, giving the 2''-O-protected kanamycin A derivative of the formula (IV''). After this, the 2''-O-protected kanamycin A derivative (IV'') is reacted with a substantially 1 molar proportion or more of a chloroformate of the formula:

wherein B'' is an alkoxycarbonyl or aralkyloxy group same as the group B' as defined above, or of an alkanoic acid or a reactive equivalent thereto, such as acetic acid, acetic chloride or acetic anhydride, in the same way as in the alkoxycarbonylation, aralkyloxycarbonylation or alkanoylation step of the aforesaid stage (c) of the process of the second aspect invention.

In the present process of the third aspect invention, the above-mentioned stage (c') is followed by the stage (d') in which the 3',4'-di-O-sulfonation of the 3',4'-dihydroxy-2''-O-protected kanamycin A compound (V') is carried out in the same way as in the stage (d) of the process of the second aspect invention, but without involving the sulfonylation of the 2'-hydroxyl group which has been blocked by the tetrahydropyranyl group. In this way, there is prepared the 3',4'-di-O-sulfonyl-kanamycin A compound of the formula (VII').

Thereafter, the 3',4'-di-O-sulfonyl-kanamycin A compound so obtained is converted into the corresponding 3'-eno-kanamycin A compound in the stage (e') of the present process by treating with an alkali metal iodide and zinc metal powder according to the Tipson-Cohen method or with sodium iodide alone in a way similarly to the stage (e) of the process of the first aspect invention. In this stage (e'), the 2"-hydroxyl group of the kanamycin A compound has been blocked, and hence the reaction of converting the 3',4'-di-O-sulfonyl-kanamycin A compound into the 3'-eno-kanamycin compound can be performed by treating with an alkali metal iodide in the presence of zinc metal powder so that the 3'-enoation can be promoted, when the undesired formation of the aziridine ring between the 2"-and 3"-carbon atoms does not take place.

Further, the 3'-eno-kanamycin A compound so obtained is converted into the corresponding 3',4'-dideoxybanamycin A compound in the stage (f') of the present process by reducing with hydrogen in the presence of a known hydrogenation catalyst to effect the hydrogenation of the 3',4'-olefinic bond into the saturated bond, in the same manner as in the stage (f) of the process of the second aspect invention.

The process of the third aspect invention includes also the stage (g') of removing the residual hydroxyl-protecting groups (X, Y and Z), the stage (h') of removing the residual amino-protecting group (B") remaining at the 6'-amino group, and the stage (i') of removing all the sulfonyl groups (A) remaining at the 1-, 3- and 3"-amino groups of the kanamycin A compound. These deprotecting stages (g'), (h') and (i') may be effected in the same manner as in the deprotecting stages (g), (h) and (i) of the process of the second aspect invention, respectively. Also in the present process, each of these stages (g'), (h') and (i') may be conducted at an appropriate time after the stage (d'), and the sequence in which each of these deprotecting stages (g'), (h') and (i') is carried out one after another may be properly chosen properly, like to the process of the second aspect invention. Accordingly, it is possible also for the present process to be carried out via anyone of the various routes mentioned hereinbefore in respect of the process of the second aspect invention. For instance, the present process may be conducted in such a way that the stage (g') of removing the residual divalent hydroxyl-protecting groups (X, Y and Z) precedes the stage (e') of converting the 3',4'-di-O-sulfonyl-kanamycin A compound into the 3'-eno-kanamycin A compound.

According to a fourth aspect of this invention, there is further provided a process for the production of 1-N-(2-hydroxy-3-aminopropionyl)- or 1-N-(2-hydroxy-4-aminobutyryl)-3',4'-dideoxykanamycin A represented by the formula (Ib) shown hereinbefore, which comprises the steps of:

(i) acylating the 1-amino group of 3',4'-dideoxykanamycin A or a partially protected derivative thereof represented by the formula (Ic):

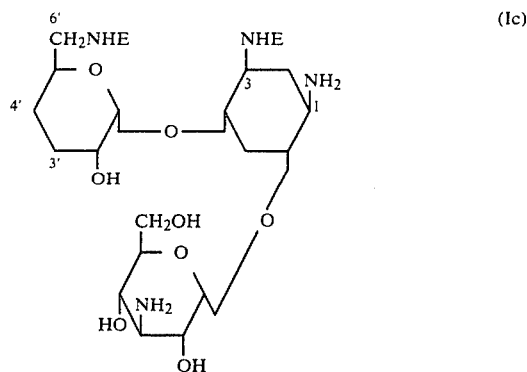

wherein each E represents hydrogen atom or an amino-protecting group, preferably an alkoxyoxycarbonyl containing 2 to 5 carbon atoms, an aralkyloxycarbonyl, specially benzyloxycarbonyl or an aryloxycarbonyl group, with an α-hydroxy-ω-aminoalkanoic acid of the formula:

wherein n is 1 or 2, or an amino-protected derivative thereof or a functional derivative thereof, to produce a 1-N-acylated compound of the formula:

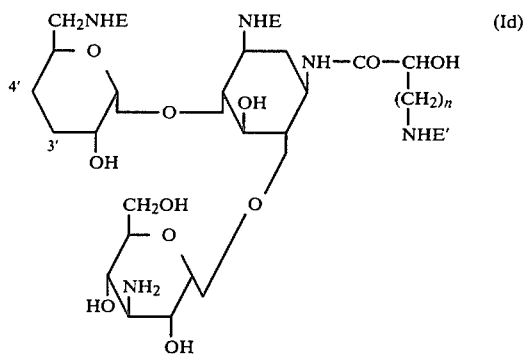

wherein E and n are as defined above and E' is hydrogen or an amino-protecting group; and (ii) removing the amino-protecting group(s) (E and E'), if remaining, from the compound of the formula (Id).

The process of the fourth aspect invention is here described in detail.

In this process, it is principally possible to employ 3',4'-dideoxykanamycin A free base or an acid-addition salt thereof as the starting material, without blocking previously the amino groups other than the 1-amino group of the kanamycin A compound. However, it is preferred to use a partially protected derivative of 3',4'-dideoxykanamycin A having some of the amino groups protected other than the 1-amino group thereof which is represented by the above formula (Ic). The amino-protecting group available for the partial protection of the amino groups of 3',4'-dideoxykanamycin A may be any of known, conventional amino-protecting groups. Typical examples of amino-protecting groups include alkyloxycarbonyl such as tert-butoxycarbonyl and tertamyloxycarbonyl; cycloalkyloxycarbonyl such as cyclohexyloxycarbonyl; aralkoxycarbonyl such as benzyloxycarbonyl; acyl such as trifluoroacetyl and o-nitrophenoxyacetyl; phosphinothioyl such as diphenylphosphinothioyl and dimethylphosphinothionyl; and phosphinyl such as diphenylphosphinyl. Divalent amino-protecting groups such as phthaloyl may also be used. Protection of amino groups in the form of a Schiff base is also utilizable. The method of introducing these amino-protecting groups into the 3- and/or 6'-amino groups of 3',4'-dideoxykanamycin A may be performed by any of processes known per se in the synthesis of peptides and other organic compounds, for example those using an acid halide, acid azide, active ester or acid anhydride as an amino-protecting group-introducing reagent, as described, for example, in U.S. Pat. No. 4,107,424. Depending upon the amount of amino-protecting group-introducing reagent used which is in the range of 0.5 to 6 molar equivalents, it is possible to produce a mixture of different, partially amino-protected derivatives of 3',4'-dideoxykanamycin A in any proportion due to the difference in reactivity among the respective amino groups of the starting compound. Mixtures of such partially amino-protected derivatives of 3',4'-dideoxykanamycin A may also be used in the acylation step (i) of the present process. It is therefore convenient for the acylation step (i) to use a crude product of the amino-protecting method which is usually a mixture of partially amino-protected derivatives of 3',4'-dideoxykanamycin A as it is without purifying it. Thus, in the method of introducing the amino-protecting group, the amino-protecting group-introducing reagent may preferably be used in an amount of 1 to 5 molar equivalent in an aqueous organic solvent.

An alternative method for the introducting of an amino-protecting group is described in our copending Japanese Patent Application No. 138402/78 filed on Nov. 11, 1978, our copending U.S. patent application Ser. No. 90,591 filed on Nov. 2, 1979 or U.K. Patent Application No. 4938894 which is relating to a "zinc-complex" process for the preparation of amino-glycosidic antibiotics having some of the amino groups selectively protected. According to this alternative method, 3',4'-dideoxykanamycin A is first converted into a complex thereof with zinc cation and then acylated into a partially amino-protected derivative.

The above-mentioned "zinc complex" process is generally concerned with a process for the production of a selectively acylated N-protected derivative of an amino-glycosidic antibiotic having a 3-aminoglycosyl or 3-alkylaminoglycosyl group linked to the 6-hydroxy group of a deoxystreptamine moiety, the process comprising the steps of:

providing an aminoglycosidic antibiotic-zinc cation complex, reacting the complex with an acylation reagent to produce the N-acylated zinc complex, that is to say, a second complex of zinc cations with the aminoglycosidic antibiotic which has non-complexed amino groups acylated, and reacting the second complex with a reagent to remove zinc cations therefrom to produce the selectively acylated N-protected derivative of the aminoglycosidic antibiotic. The amino-glycosidic antibiotic-zinc cation complex may be provided by reacting the aminoglycosidic antibiotic with a zinc salt in an inert organic solvent. According to this "zinc complex" process, from 3',4'-dideoxykanamycin A to be employed as the initial material in the process of the fourth aspect invention may be prepared in a facile and efficient way a partially protected derivative of 3',4'-dideoxykanamycin A, for example, by the following procedure: Thus, 3',4'-dideoxykanamycin A is dissolved or suspended in an appropriate organic solvent or aqueous organic solvent, and to the resulting solution or suspension is added a suitable zinc salt in a quantity of at least 1 mol per mol of 3',4'-dideoxykanamycin A. Any ordinary organic solvent may be employed for this purpose, as far as the zinc complex formed after the addition of the zinc salt is at least partially soluble in it. However, use of a large volume of a polar organic solvent and particularly of greater volume of water should preferably be avoided, because the presence of polar organic solvent and water is likely to reduce the stability of the resulting aminoglycoside-zinc cation complex formed, so that the subsequent acylation reaction for introduction of the amino-protecting group is likely to give unsatisfactory result.

Thus, it is desirable to use an organic solvent of high solvent power such as dimethylsulfoxide for the solvent in which the zinc complex is to be formed, but it is feasible to employ aqueous dimethylsulfoxide, dimethylformamide, aqueous dimethylformamide, a mixture of dimethylsulfoxide and dimethylformamide, tetrahydrofuran, aqueous tetrahydrofuran, and even a lower alkanol such as methanol, ethanol and aqoue methanol.

Zinc cation may be supplied in the form of a zinc salt to the reaction system where the zinc complex is formed. Any zinc salt which is formed by reaction of zinc cation with an ordinary inorganic or organic acid may be used for the present purpose. In general, however, it is desirable to employ a zinc salt of a weak acid, such as zinc acetate.

As long as the total molar quantity of zinc salt used is at least equal to the molar quantity of the aminoglycosidic antibiotic, the complexing reaction may proceed. However, it is preferable to use the zinc salt in a quantity of substantially more than 1 mol per mol of the aminoglycosidic antibiotic, so that the equilibrium of the complexing reaction is shifted in favor of the formation of the zinc complex. Favorable yield of the zinc complex may be obtained when using the zinc salt in a quantity of about 2.3–6 mol per mol of the aminoglycoside, but in practice it is most preferable to use the zinc salt in a quantity of 4–5 mol per mol of the aminoglycoside. Time required for complete complexing reaction after the addition of the zinc salt may vary depending on the nature of the organic solvent used, and it may be in the range of "instantaneously" (when using aqueous organic solvent) to 20 hours. The complexing reaction normally may proceed at ambient temperature, but heating or cooling may be done.

In this way, a solution of suspension containing the zinc complex of the aminoglycoside is prepared, to which is then added an acylation reagent having an acyl group to be introduced as the amino-protecting group.

The acylation reagent employed for this purpose of introducing the amino-protecting groups may be a usual amino-protecting reagent, and this is used to ensure that the non-complexed 3- and 6'-amino groups in the resultant 3',4'-dideoxykanamycin A-zinc cation complex are acylated by and blocked with the acyl group of the acylation reagent. The acyl group available in this invention may be an alkoxycarbonyl group, an aralkyloxycarbonyl group or an aryloxycarbonyl group or an arylsulfonyl group which are all the conventional amino-protecting group. The acylation reagent available for this purpose may either be a chloroformate of the following general formula

   (Xa)

wherein $R^3$ is hydrogen, an alkyl group, particularly an alkyl group of 1–6 carbon atoms, an aryl group, particularly phenyl, or an aralkyl group, especially benzyl, and these groups being occasionally further substituted, or a p-nitrophenyl carbonate of the following general formula:

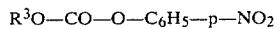   (Xb)

or active N-hydroxysuccinimide ester of the following formula:

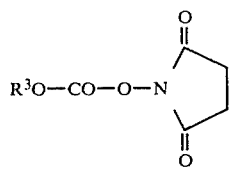   (Xc)

or an azidoformate of the following formula:

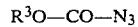   (Xd)

where $R^3$ is as defined above; or a sulfonic acid of the following formula:

   (Xe)

wherein $R^4$ is an aryl group such as phenyl, either substituted or unsubstituted, or an acid halide, acid anhydride or active ester of said sulfonic acid.

Particular examples of the available acylation reagent include p-nitrophenyl formate, p-nitrophenol ester of trifluoroacetic acid, trifluoroacetic acid ester, N-benzyloxycarbonyloxysuccinimide (a representative active ester), N-benzyloxycarbonyloxyphthalimide, benzyloxycarbonyl chloride, p-methoxybenzyloxycarbonyloxy-p-nitrophenyl, t-butoxycarbonylazide, phenoxycarbonyl chloride, tosyl chloride, mesyl chloride and others.

The acylation reagent, either as such or as a solution in a solvent such as tetrahydrofuran and dimethylsulfoxide or in a mixture of these solvents, may be added to the solution or suspension containing the aminoglycoside-zinc complex. The molar quantity of the acylation reagent added may usually be equal to or a little excessive than the number of the non-complexed amino groups with which the acylation reagent is to react. In some cases, however, the molar quantity of the acylation reagent added may be up to a molar quantity of about 3 times higher than the number of the non-complexed amino groups. The acylation reagent may be added either at once or in portions slowly over a duration of 2–3 hours, though it may usually be added over a time of 30 minutes to 1 hour. The acylation may be conducted at a temperature of −20° C. to 100° C. but may normally be effected at a temperature ranging from 0° C. to ambient temperature. In some cases, the reaction temperature may be kept low at the time of addition of the acylation reagent and be then elevated gradually as the acylation proceeds. Normally, the acylation reaction may be effected in situ in the organic solvent in which the aminoglycosidic antibiotic-zinc cation complex was formed. This acylation of the zinc complex produces the N-acylated zinc complex (the aforesaid second complex), that is, the complex of zinc cations with the selectively N-acylated aminoglycosidic antibiotic derivative.

According to the "zinc complex" process stated above, the step of the acylation of the aminoglycoside-zinc cation complex is followed by the step of removing zinc cation from the second complex, ie. the N-acylated zinc complex (namely, destroying of the zinc complex) to yield the selectively protected N-acylated derivative of the aminoglycoside which is free from zinc cations.

For removal of zinc cation from the second complex ie. the N-acylated zinc complex, it is necessary to treat the N-acylated zinc complex with a suitable reagent which removes zinc cation from said N-acylated zinc complex. For this purpose, there are many available methods. The first method is to react a zinc-precipitating agent, which is capable of converting zinc cation into a water-insoluble zinc compound such as zinc sulfide, zinc hydroxide or zinc carbonate while the N-acylated zinc complex is still remaining dissolved in the acylation reaction mixture where the aminoglycosidic antibiotic-zinc cation complex has been acylated, or after it is transferred into a new solution in a fresh volume of an organic solvent from said acylation reaction mixture.

The zinc-precipitating agent available in the first method include hydrogen sulfide, an alkali metal sulfide such as sodium sulfide, ammonium sulfide, an alkaline earth metal sulfide such as calcium sulfide and an alkali metal carbonate such as sodium carbonate or ammonium hydroxide. A second method is (i) to concentrate or concentrate to dryness by evaporation of the solvent or (ii) to dilute with a liquid diluent the aforesaid acylation reaction mixture or the new solution of the N-acylated zinc complex transferred into the fresh volume of the organic solvent so as to give an oily or solid deposit, concentrate or residue, followed by recovering the desired N-acylated aminoglycosidic antibiotic derivative from said deposit, concentrate or residue in any way. The liquid diluent available in this second method is water or a such an organic liquid in which the N-acylated zinc complex as the whole or the N-acylated aminoglycosidic antibiotic derivative moiety of said N-acylated zinc complex has no or little solubility.

The second complex of zinc cations with the selectively N-acylated aminoglycosidic antibiotic derivative once separated may be admixed with water or a polar organic solvent, either anhydrous or aqueous, which serves as the zinc cation-removing reagent. This polar organic solvent is either such one in which the zinc salt is soluble but in which the N-acylated aminoglycosidic antibiotic derivative is insoluble, or such one in which the zinc salt is insoluble but in which the N-acylated aminoglycosidic antibiotic derivative is soluble.

The second complex of zinc cations with the N-acylated aminoglycosidic antibiotic derivative once separated may be again dissolved wholly in an organic solvent containing a proportion of water, and the resulting solution is subjected to a chromatographic procedure using a cation-exchange resin, an anion-exchange resin, chelate-exchange resin or a water-insoluble polymer containing functional groups capable of combining with a metal, which serves as the zinc cation-removing reagent.

The acylation reaction mixture may be directly passed through a column of a cation-exchange resin, an anion-exchange resin, chelate-exchange resin or a water-insoluble polymer containing the metal-combining functions for adsorption of the second complex of zinc cations with the N-acylated aminoglycosidic antibiotic derivative, and the column is then developed with an aqueous organic solvent containing or not containing an amount of acid or base, and the eluate is collected in fractions, followed by recovery of the fractions containing the desired selectively N-acylated aminoglycosidic antibiotic derivative but containing no zinc cations.

When the desired N-acylated aminoglycosidic antibiotic derivative is insoluble or substantially insoluble in water, the acylation reaction mixture may be immediately admixed with water, so that said derivative is precipitated separately from the zinc salt remaining dissolved in water.

In the zinc complex formed in the above-mentioned "zinc complex" process, zinc cations are principally complexing with 1-amino and 3''-amino groups of the aminoglycosidic antibiotic, and hence the N-acylation of the aminoglycosidic antibiotic-zinc cation complex followed by the removal of zinc cations therefrom normally gives the N-acylated aminoglycosidic antibiotic derivative in which amino group other than 1-amino and 3''-amino groups are protected by the acyl group. When the N-acylated aminoglycosidic antibiotic derivative so obtained from the "zinc complex" process may then be 1-N-acylated with an α-hydroxy-ω-aminoalkanoic acid of the formula (IX) according to the fourth aspect invention.

It may be added that the above-mentioned "zinc complex" process may be applied to the preparation of the protected derivative of kanamycin A of the formula (II) which is to be used as the initial material in the process of the second or third aspect of this invention. Moreover, the partially protected derivative of kanamycin A or 3',4'-dideoxykanamycin A which are to be used as the starting material in the processes of this invention may be prepared also by utilizing the method of Nagabhushan et al as set forth in U.S. Pat. No. 4,136,254.

In the first step (i) of the process according to the fourth aspect of this invention, the 1-amino group of 3',4'-dideoxykanamycin A or a partially protected derivative thereof is acylated by reacting with an α-hydroxy-ω-aminoalkanoic acid of the formula (IX), particularly 3-amino-2-hydroxypropionic acid (as DL-isoserine, D-isoserine or L-isoserine) or L-4-amino-2-hydroxybutyric acid to acylate 1-amino group with the 3-amino-2-hydroxypropionyl or 4-amino-2-hydroxybutyryl group. This 1-N-acylation may be conducted generally as described eg. in the specification of U.S. Pat. Nos. 3,781,268; 4,001,208 and 4,107,424 or U.K. Pat. No. 1,426,908 according to any known method of synthesis of amides by reacting with an isoserine or L-4-amino-2-hydroxybutyric acid, either in its free acid form or in the form of its reactive equivalent such as an active ester, eg. the dicyclohexylcarbodiimide ester, mixed acid anhydride, acid azide in an inert organic solvent such as dioxane, dimethoxyethane, dimethylformamide, tetrahydrofuran or aqueous ones of these solvents. Isoserine and L-4-amino-2-hydroxybutyric acid may be such ones of which amino group has been blocked with an amino-protecting group. Suitable amino-protecting group for this purposes may be the same as or different from that one which was used for the preparation of the partially protected derivative of 3',4'-dideoxykanamycin A to be 1-N-acylated. t-Butoxycarbonyl group is a preferred amino-protecting group, as it is readily removably by treating with a dilute acid such as aqueous trifluoroacetic acid, aqueous acetic acid and diluted hydrochloric acid. Benzyloxycarbonyl group which is removed by conventional catalytic hydrogenolysis over palladium or platinum oxide catalyst, as well as phthaloyl group which is easily removed by hydrolysis with hydrazine are very convenient as the amino-protecting group to this end.

The acylating reaction in the 1-N-acylation step (i) of the process of the fourth aspect invention may preferably be conducted in an aqueous organic solvent using an active ester of the α-hydroxy-ω-aminoalkanoic acid (IX). The suitable active ester may be N-hydroxysuccinimide ester of isoserine or L-4-benzyloxycarbonylamino-2-hydroxybutyric acid, and this active ester may be employed in a quantity of 0.5 to 2 mol., favorably of 1 to 1.5 mol per mol of the 3',4'-kanamycin A to be 1-N-acylated. The water-miscible organic solvent for use in the reaction medium may preferably be dioxane, dimethoxyethane, dimethylformamide, tetrahydrofuran.

Subsequently to the above step (i), the N-deprotection step (ii) of the present process is carried out to remove all the residual amino-protecting groups from the 1-N-acylation product (Id) obtained in the above step (i). The removal of the residual amino-protecting group may be achieved by a conventional N-deprotecting technique. Such a residual amino-protecting group which is of an alkoxycarbonyl type may be removed by hydrolysis with an aqueous solution of trifluoroacetic acid or acetic acid or with a diluted acid solution such as dilute hydrochloric acid. Such a residual amino-protecting group which is of an aralkyloxycarbonyl type, for example, benzyloxycarbonyl is readily removed by conventional catalytic hydrogenolysis. When all the residual amino-protecting groups are removed from the 1-N-acylation product of the step (i) of the present process, the desired 1-N-(2-hydroxy-3-aminopropionyl)- or 1-N-(2-hydroxy-4-aminobutyryl)-3',4'-dideoxykanamycin A of the formula (Ib) is obtained in a high yield.

The new compounds of the formula (I) according to the first aspect invention, and particularly 3',4'-dideoxykanamycin A, 1-N-(2-hydroxy-3-aminopropionyl)-3',4'-dideoxykanamycin A and 1-N-(L-2-hydroxy-4-aminobutyryl)-3',4'-dideoxykanamycin A as well as an acid-addition salt thereof are of a very low toxicity and useful as antibacterial agent as stated hereinbefore. The new compounds of this invention and their pharmaceutically acceptable acid-addition salt may be administered orally, intraperitoneally, intravenously, subcutaneously or intramuscularly using any pharmaceutical form known to the art for such administration and in a similar manner to the known kanamycins. For instance, the new compounds of this invention may be administered orally using any pharmaceutical form known to the art for oral administration. Examples of the pharmaceutical forms for oral administration are powders, capsules, tablets, syrup and the like. A suitable dose of the new compounds of this invention for effective treatment of bacterial infections is in a range of 0.5 to 4 g. per person a day when it given orally. It is preferred that said dose should be orally administered in three to four aliquots per day. The new compounds of this invention may also be administered by intramuscular injection at a dosage of 200 to 2000 mg per person two to four times per day. Moreover, the new compounds of this invention may be formulated into an ointment for external application which contains the active compound at a concentration of 0.5–5% by weight in mixture with a known ointment base such as polyethylene glycol. Furthermore, the new compounds of this invention are useful for sterilization of surgical instruments.

According to a fifth aspect of this invention, therefore, there is provided a pharmaceutical composition comprising a safe and antibacterially effective amount of a new compound of this invention selected from 3',4'-dideoxykanamycin A; 1-N-(2-hydroxy-3-aminopropionyl)-3',4'-dideoxykanamycin A; 1-N-(L-2-hydroxy-4-aminobutyryl)-3',4'-dideoxykanamycin A; and a pharmaceutically acceptable acid-addition salt thereof, as the active ingredient, in combination with a pharmaceutically acceptable carrier for the active ingredient. In the pharmaceutical composition of this invention, the active ingredient compound may be incorporated in an amount of 0.5% to 50% by weight of the whole composition.

According to another aspect of this invention, there is provided a method for inhibiting bacterial growth which comprises administering an antibacterially effective and safe amount of a new compound of this invention according to the aforesaid formula (I) to an animal susceptible to the bacterial growth. There is further provided a method for inhibiting in vitro bacterial growth, which comprises contacting a surface susceptible to said bacterial growth, with an antibacterially effective amount of a compound of this invention.

In the course of the production of 3',4'-dideoxykanamycin A according to the process of the second or third invention, there are formed the various intermediate products which are new and useful for the conversion into 3',4'-dideoxykanamycin A in accordance with the processes of this invention. According to another aspect of this invention, therefore, there is provided as a new intermediate a compound of the formula:

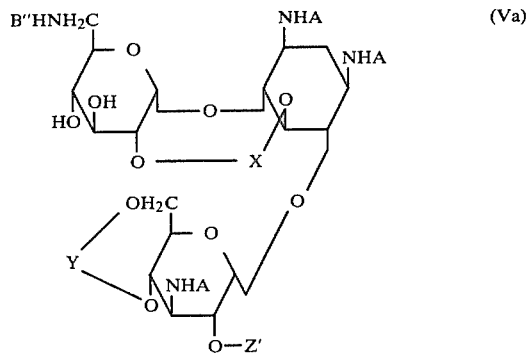

(Va)

wherein each A represents an alkylsulfonyl group containing 1 to 4 carbon atoms, an arylsulfonyl group, specially tosyl, or an aralkylsulfonyl group, specially benzylsulfonyl group; B" represents an alkoxycarbonyl group containing 2 to 5 carbon atoms, an aralkyloxycarbonyl group, specially benzyloxycarbonyl; or an aryloxycarbonyl group; X represents isopropylidene, cyclohexylidene, benzylidene or tetrahydro-4-pyranylidene group; Y represents an alkylidene group containing 1 to 6 carbon atoms, specially isopropylidene, cyclohexylidene, bezylidene or tetrahydro-4-pyranylidene group; and Z' is a hydrogen atom or tetrahydropyranyl group. The intermediate compound of the formula (Va) includes particularly 6'-N-benzyloxycarbonyl-1,3,3''-tri-N-tosyl-5,2'-O-isopropylidene-4'',6''-O-cyclohexylidene-kanamycin A; and 6'-N-benzyloxycarbonyl-1,3,3''-tri-N-tosyl-5,2'-O-isopropylidene-4'',6''-O-cyclohexylidene-2''-O-tetrahydropyranylkanamycin A.

This invention is now described with reference to Example 1 which is illustrative of the process of the second aspect invention, to Examples 2 and 3 which are illustrative of the process of the third aspect invention, and to Examples 4 and 5 which are illustrative of the process of the fourth aspect invention.

EXAMPLE 1

Synthesis of 3',4'-dideoxykanamycin A (1) Preparation of 6'-N-benzyloxycarbonyl-1,3,3''-tri-N-tosylkanamycin A 6'-N-Benzyloxycarbonylkanamycin A (free base) (1.79 g) (see the aforesaid "Journal of Antibiotics" Vol. 25, 695–708 (1972)) and anhydrous sodium carbonate (1.1 g) were dissolved in 50 ml of a mixture of water and dioxane (1:3 by volume), and to the resulting solution was added 2.0 g of p-toluenesulfonyl chloride under stirring. The admixture so obtained continued to be stirred at ambient temperature overnight (for the tri-N-tosylation) and then concentrated to a smaller volume. The concentrated solution was admixed with a volume of water, and the precipitate so deposited was removed by filtration, washed with ethyl ether and dried to give the above titled product as a solid. Yield 3.14 g (98%). $[\alpha]_D^{25} + 10°$ (c 0.4, acetone).

Elemental analysis: Found: C, 52.10; H, 5.56; N, 5.12; S, 8.68%. Calcd. (for $C_{47}H_{60}N_4O_{19}S$): C, 52.21; H, 5.59; N, 5.18; S, 8.90%.

(2) Preparation of 6'-N-benzyloxycarbonyl-4'',6''-O-cyclohexylidene-1,3,3''-tri-N-tosylkanamycin A The substance (1.29 g) obtained in the above procedure (1) was taken up into 4 ml of dimethylformamide, and the resulting solution was admixed with 45 mg of toluenesulfonic acid and 0.86 ml of 1,1-dimethoxycyclohexane. The admixture so obtained was allowed to stand at ambient temperature for 6 hours (for the 4'',6''-O-cyclohexylidenation). The reaction mixture was then poured into a large volume of a solution of sodium hydrogen carbonate in water, and the precipitate so deposited was removed by centrifugation, well washed with water and then dried. Yield 1.35 g (98%). $[\alpha]_D^{25} + 0°$ (c 0.5, acetone).

Elemental analysis: Found: C, 54.89; H, 6.10; N, 4.63; S, 8.52%. Calcd.: (for $C_{53}H_{68}N_4O_{19}S_3$): C, 54.81; H, 5.90; N, 4.82; S, 8.28%.

(3) Preparation of 4″,6″-O-cyclohexylidene-1,3,3″-tri-N-tosyl-4′-0:6′-N-carbonyl-kanamycin A

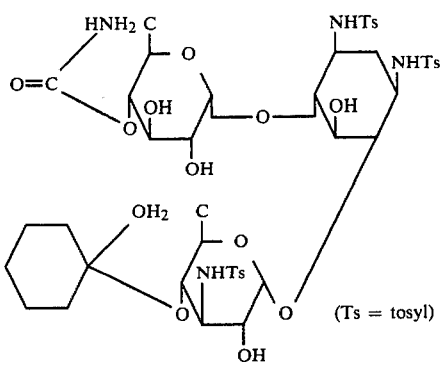

(Ts = tosyl)

The substance (911 mg) obtained in the above procedure (2) was dissolved in 18 ml of dimethylformamide, and to the resultant solution was added 337 mg of 50% sodium hydride in oil. The admixture was agitated overnight at ambient temperature and then admixed with 3.5 ml of 4 N acetic acid and further with 50 ml of toluene. The whole admixture was distilled to remove the solvents, and the thick syrup so obtained was admixed with a large volume of water. The precipitate so deposited was collected by filtration, washed with ethyl ether and dried to give a colorless solid comprising the above titled compound. Yield 685 mg (85%).

(4) 4″,6″-O-cyclohexylidene-4′-0:6′-N-carbonyl-5,2′-O-isopropylidene-1,3,3″-tri-N-tosylkanamycin A

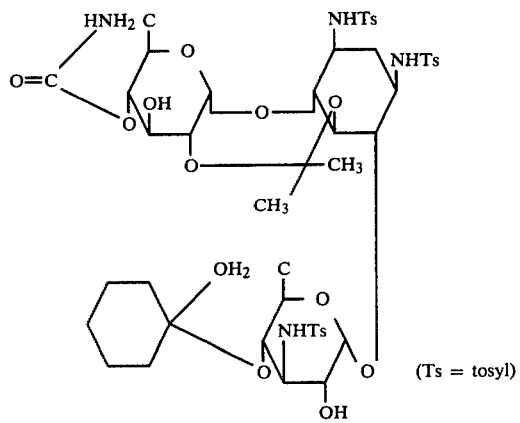

(Ts = tosyl)

The substance (100 mg) obtained in the above procedure (3) was suspended in a mixture of 4 ml of dichloromethane and 2.5 ml of tetrahydrofuran, and to the resulting suspension was added 2 ml of 2,2-dimethoxypropane. The admixture so obtained was further mixed with 6 ml of a solution of 0.035 N hydrogen chloride in dichloromethane, followed by heating for 17 minutes under reflux (for the 5,2′-O-isopropylidenation). This reaction was conducted in a reactor vessel fitted with a reflux column at the top of the reactor vessel where a column containing 5 ml of "Molecular Sieves 5A" (a product of zeolite produced by Union Carbide Co., U.S.A.) was interposed between the bottom of the reflux column and an outlet opening in the top of the reactor vessel in such a way that the vapour distilled from the reaction solution present in the vessel could arise through a side-armed tube which was connected directly between the reaction vessel and the bottom of the reflux column, so that the condensed vapour containing methanol falling down in the reflux column could then pass via the column of molecular sieves and so that only methanol could be removed by adsorption by the molecular sieves. Thus, the condensed solvent freed from methanol could again come back into the reaction vessel. If the above reaction solution was heated simply under reflux without removing the methanol vapour by means of said molecular sieve column, the undesired 2′,3′-O-isopropylidene derivative was by-produced in a very higher proportion than the desired 5,2′-O-isopropylidene derivative, so that the latter product desired was formed in a very poor yield and could not be recovered in a substantial yield.

The reaction mixture from the above reaction was cooled by ice-cooling and then poured into a large volume of a mixture of dioxane and 1 N aqueous ammonia, and the resulting mixture was concentrated. The concentrated solution so obtained was diluted with a volume of ethyl ether to precipitate a colorless solid. This solid was collected by filtration, washed with water and dried to give 85 mg of a solid. This solid was taken up into 3 ml of chloroform and the resultant solution was chromatographed in a column of 5 ml of silica gel developed with chloroform-ethanol (10:1 by volume) as the eluent for a purification purpose. The effluent running out of the silica gel column was concentrated to dryness in vacuo to give 61 mg of a solid. This solid was again taken up into 5 ml of chloroform, and the solution was heated. As the heating proceeded, the undesired 2′,3′-O-isopropylidene derivative became deposted. The whole solution was allowed to stand at ambient temperature overnight, followed by filtration. The filtrate so obtained was concentrated to dryness, giving 32 mg of the above titled desired product. $[\alpha]_D^{25}+20°$ (c 0.5, acetone).

Elemental analysis: Found: C, 53.61; H, 5.81; N, 4.88; S, 8.57%. Calcd. (for $C_{49}H_{64}N_4O_{18}S_3$): C, 53.83; H, 5.90; N, 5.13; S, 8.80%.

(5) Preparation of 6′-N-benzyloxycarbonyl-1,3,3″-tri-N-tosyl-5,2′-O-isopropylidene-4″,6″-O-cyclohexylidenekanamycin A The substance (48 mg) obtained in the above procedure (4) was dissolved in 2 ml of water-dioxane (1:3 by volume), and the solution so obtained was admixed with 30 mg of anhydrous sodium carbonate, followed by heating at 50° C. for 1 hour to effect the hydrolysis of said substance which brought about the fission of the 4′,6′-cyclic carbamate and the removal of the 4′,-0:6′-N-carbonyl group. The resulting reaction solution was then immediately admixed with 80 mg of benzyloxycarbonyl chloride, followed by allowing to stand for 2 hours at ambient temperature (for the 6′-N-benzyloxycarbonylation). The reaction mixture was then neutralized to weakly alkaline by addition of acetic acid, and it was subsequently concentrated to a smaller volume in vacuo. The concentrated solution was admixed with a large volume of water and the solid deposited was removed by filtration, well washed with water and then ethyl ether and dried, affording the above captioned product as a solid. Yield 42 mg (82%). $[\alpha]_D^{25}+9°$ (c 1, chloroform).

Elemental analysis: Found: C, 55.75; H, 6.07; N, 4.48; S, 7.82%. Calcd. (for $C_{56}H_{72}N_4O_{19}S_3$): C, 55.99; H, 6.04; N, 4.66; S, 8.01%.

(6) Preparation of 6'-N-benzyloxycarbonyl-1,3,3''-tri-N-tosyl-5,2'-O-isopropylidene-4'',6''-O-cyclohexylidene-3',4',2''-tri-O-benzylsulfonyl-kanamycin A

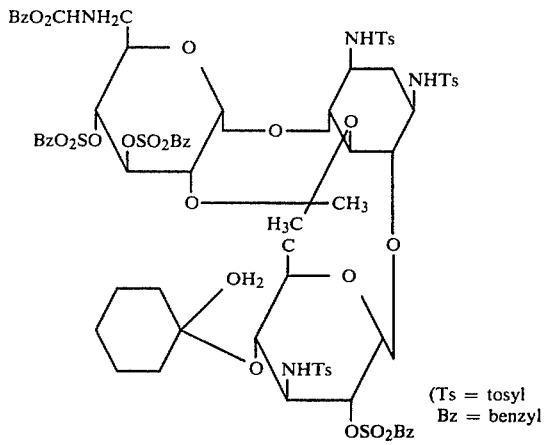

(Ts = tosyl
Bz = benzyl)

6'-N-Benzyloxycarbonyl-1,3,3''-tri-N-tosyl-4,2'-O-isopropylidene-4'',6''-O-cyclohexylidene-kanamycin A (611 mg) obtained in the above procedure (5) was dissolved in 12 ml of pyridine, and the resulting solution after ice-cooling was admixed with 320 mg of benzylsulfonyl chloride and then allowed to stand for 2 hours under ice-cooling (for the 3',4'-di-O-benzylsulfonylation accompanied by 2''-O-benzylsulfonation). The liquid reaction mixture was admixed with 0.2 ml of water and concentrated to a smaller volume in vacuo. The residual solid was admixed with a volume of water, and the insoluble solid was removed by filtration, washed well with water and dried, giving the above titled product as a solid. Yield 795 mg (94%). $[\alpha]_D^{25} + 70°$ (c 1, chloroform).

Elemental analysis Found: C, 55.23; H, 5.40; N, 3.19. Calcd. (for $C_{77}H_{90}N_4O_{25}S_6$): C, 55.58; H, 5.45; N, 3.37%.

(7) Preparation of 6'-N-benzyloxycarbonyl-1,3,3''-tri-N-tosyl-5,2'-O-isopropylidene-4'',6''-O-cyclohexylidene-2''-O-benxylsulfonyl-3',4'-dideoxy-3'-eno-kanamycin A

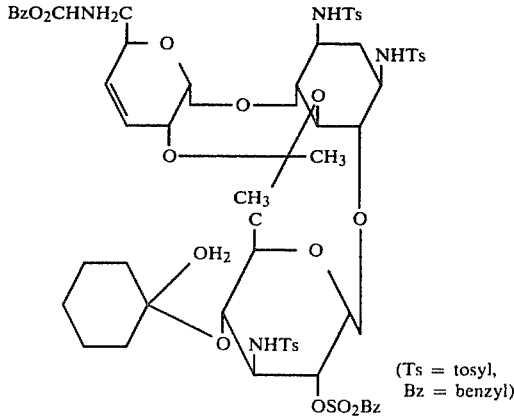

(Ts = tosyl,
Bz = benzyl)

The 3',4',2''-tri-O-benzylsulfonyl-kanamycin A derivative (560 mg) obtained in the above procedure (6) was dissolved in 12 ml of dimethylformamide, and the resulting solution was admixed with 6 g of sodium iodide, followed by heating at 100° C. for 5.5 hours (for the 3',4'-unsaturation). The reaction mixture was admixed with a large volume of chloroform, followed by centrifugation. The supernatant solution so obtained was concentrated to a smaller volume and diluted with a volume of water, and the solid deposited was well washed with water and then dried. The solid obtained was taken up in 10 ml of chloroform and then purified by chromatographing on a silica gel column developed with chloroform-methanol (20:1) as the eluent. Concentration of the effluent from the silica gel column to dryness gave the above titled compound as a solid. Yield 218 mg (49%). $[\alpha]_D^{25} + 11°$ (c 1, chloroform).

Elemental analysis Found: C, 57.11; H, 5.66; N, 4.09; S, 9.43%. Calcd. (for $C_{63}H_{76}N_4O_{19}S_4$): C, 57.25; H, 5.80; N, 4.24; S, 9.70%.

(8) Production of 3',4'-dideoxykanamycin A

The 3'-eno-kanamycin A derivative (453 mg) obtained in the above procedure (7) was dissolved in 7 ml of 80% aqueous acetic acid, followed by heating at 80° C. for 1 hour (for the removal of the 5,2'-O-isopropylidene and of the 4'',6''-O-cyclohexylidene groups). The reaction solution was concentrated to a smaller volume and the concentrated solution was admixed with water to deposit a solid which was subsequently washed with water and then dried. The solid so obtained was comprising the de-isopropylidenated and de-cyclohexylidenated kanamycin A derivative, that is, 6'-N-benzyloxycarbonyl-1,3,3''-tri-N-tosyl-2''-O-benzyl-sulfonyl-3',4'-dideoxy-3'-eno-kanamycin A. 413 mg of this solid product was taken up into 4 ml of dioxane, and the resulting solution was shaken under the atmosphere of hydrogen gas at 3 atm., for 2.5 hours at ambient temperature in the presence of 40 mg of platinum oxide added thereto. The reaction solution was filtered to remove the catalyst, and the filtrate was concentrated to dryness in vacuo to give 412 mg of a solid.

This treatment with hydrogen was to hydrogenate the 3',4'-unsaturated bond with hydrogen into the saturated bond and concurrently to remove the 6'-N-benzyloxycarbonyl group. The solid obtained was identified to comprise 1,3,3''-tri-N-tosyl-2''-O-benzylsulfonyl-3',4'-dideoxykanamycin A. The solid obtained was dissolved in about 150 ml of liquid ammonia at −50° C., followed by addition of 400 mg of pieces of metal sodium and by agitation at the same temperature as above for 1.5 hours (for the removal of the N-tosyl groups and the 2''-O-benzylsulfonyl group). Thereafter, to the reaction solution in liquid ammonia was added a volume of methanol, and the admixture was slowly brought to ambient temperature with evaporation of ammonia and subsequently was subjected to a reduced pressre to expell the residual trace amount of ammonia to evaporate off therefrom. The solid residue so obtained was dissolved in water and the aqueous solution obtained was neutralized by adding thereto an amount of a strongly acidic cation-exchange resin, Dowex 50W×2 (H+ form) (a product of Dow Chemical Co., U.S.A.). This resin was removed from the aqueous solution by filtration and then packed into a column, followed by development with 1 N aqueous ammonia. The eluate was collected in fractions, and the fractions containing the substance which was positive to the reaction with ninhydrin were combined together and concentrated to dryness, giving a crude product of 3',4'-dideoxykanamycin A. For purification, the solid, crude product was dissolved in water and the aqueous solution obtained was charged into a column of CM-Sephadex C-25 (a product of Pharmacia Fine Co., Sweden), followed by gradient development with 0 N→0.12 N aqueous ammonia. The eluate containing the aimed product was collected and concentrated to dryness in vacuo to give a pure product of 3',4'-dideoxykanamycin A carbonate as a colorless solid. Yield 115 mg (64%). $[\alpha]_D^{25}+116°$ (c 1, water).

Elemental analysis: Found: C, 44.22; H, 7.34; N, 10.45%. Calcd. (for $C_{18}H_{36}N_4O_9 \cdot 1.1H_2CO_3$) C, 43.90; H, 7.41; N, 10.72%.

EXAMPLE 2

Synthesis of 3',4'-dideoxykanamycin A (1) Preparation of 3',2''-di-O-acetyl-4'',6''-O-cyclohexylidene-4'-0:6'-N-carbonyl-5,2'-O-isopropylidene-1,3,3''-tri-N-tosylkanamycin A

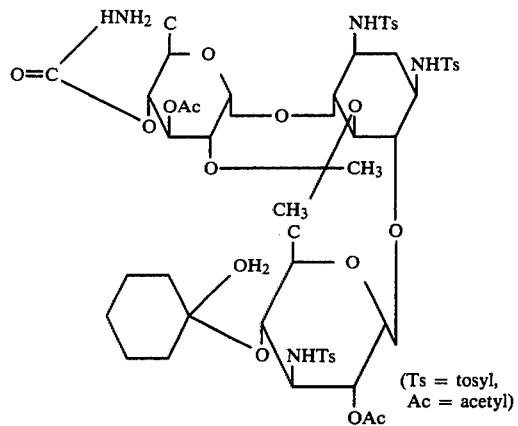

(Ts = tosyl, Ac = acetyl)

The kanamycin A derivative obtained in the above Example 1, the procedure (4), that is, 4'',6''-O-cyclohexylidene-4'-0:6'-N-carbonyl-5,2'-O-isopropylidene-1,3,3''-tri-N-tosyl-kanamycin A (210 mg) was dissolved in 4.2 ml of pyridine, and the resulting solution in pyridine was admixed with 0.11 ml of acetic anhydride, followed by allowing to stand at ambient temperature overnight (for the 3',2''-di-O-acetylation). The reaction solution was concentrated to a smaller volume and then diluted with water to deposit a precipitate which was subsequently removed by filtration, well washed with water and dried. There was afforded the above titled product as a colorless solid. Yield 217 mg (96%). $[\alpha]+76°$ (c 0.4, acetone).

Elemental analysis Found: C, 54.00; H, 5.96; N, 4.56; S, 7.78%. Calcd. (for $C_{53}H_{68}N_4O_{20}S_3$): C, 54.07; H, 5.82; N, 4.76; S, 8.17%.

N.M.R. spectrum (in deutero-pyridine): δ5.37 (triplet, J=9.5 Hz, H-3'); 5.57 (double triplet, J=9.5 & 3 Hz, H-2''); 5.85 (doublet, J=3 Hz, H-1'); 6.65 (doublet, J=3 Hz, H-1'').

(2) Preparation of 3'-O-acetyl-4'',6''-O-cyclohexylidene-4'-0:6'-N-carbonyl-5,2'-O-isopropylidene-1,3,3''-tri-N-tosyl-kanamycin A The kanamycin A derivative (29.6 mg) obtained in the above procedure (1) was dissolved in 2.5 ml of a solution of 8 N ammonia in ethanol, and the resulting solution was allowed to stand for 40 minutes at ambient temperature to effect a partial hydrolysis for the removal of the 2''-O-acetyl group. The reaction solution was immediately concentrated to a smaller volume in vacuo, and the residual concentrated solution was admixed with a volume of water to deposit a precipitate which was then removed by filtration, washed with water and dried. The above titled product was obtained as a solid in a yield of 28.5 mg (100%).

N.M.R. spectrum (in deutero-pyridine): δ5.40 (triplet, J=10 Hz, H-3').

(3) Preparation of 6'-N-benzyloxycarbonyl-4'',6''-O-cyclohexyidene-5,2'-O-isopropylidene-2''-O-tetrahydropyranyl-1,3,3''-tri-N-tosyl-kanamycin A

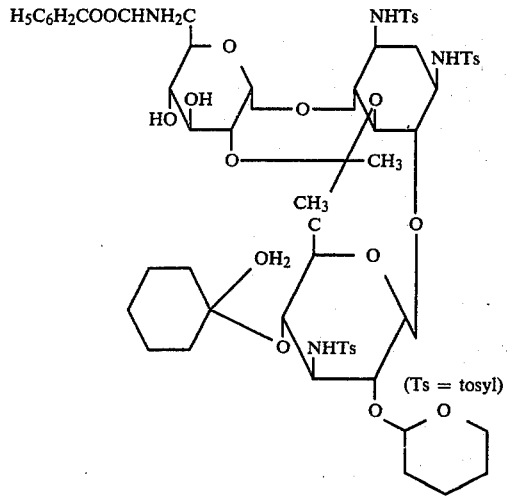

(Ts = tosyl)

The 3'-O-acetyl-kanamycin A derivative (50.5 mg) obtained in the above procedure (2) was taken up into 0.7 ml of dichloromethane, and the resulting solution was admixed with 0.86 mg of toluenesulfonic acid and then with 0.1 ml of 3,4-dihydro-2-H-pyran, followed by allowing to stand for 3 hours at ambient temperature (for the 2''-O-tetrahydropyranylation). The reaction solution was then admixed with 0.02 ml of triethylamine and concentrated to dryness, and the residue was dissolved in a volume of chloroform. The solution so obtained was washed with an aqueous solution of sodium hydrogen carbonate and dried over anhydrous sodium sulfate. The solution in chloroform was filtered to remove the sodium sulfate, and the filtrate solution was concentrated to dryness. The residual solid comprising the 2''-O-tetrahydropyranyl product was taken up into 2 ml of water-dioxane (1:3), and the resulting solution was heated at 50° C. for 1 hour after 30 mg of anhydrous sodium carbonate was added thereto. This treatment brought about the hydrolytic removal of the 3'-O-acetyl group and the removal of the 4'-0:6'-N-carbonyl group, involving in the fission of the 4',6'-cyclic carbamate ring. The reaction solution was subsequently admixed with 9.0 mg of benzyloxycarbonyl chloride, followed by allowing to stand for 2 hours at ambient temperature (for the 6'-N-benzyloxycarbonylation). The reaction mixture so obtained was neutralized to weakly alkaline by addition of acetic acid, and it was then concentrated to a smaller volume. The concentrated solution was mixed with a large volume of water and the solid so deposited was well washed with water and then with ethyl ether and dried to give 42.3 mg (yield 74%) of the above titled compound as a solid. $[\alpha]_D^{25} +28°$ (c 0.5, chloroform).

Elemental analysis Found: C, 56.65; H, 6.27; N, 4.17; S, 7.25%. Calcd. (for $C_{61}H_{80}N_4O_{20}S_3$): C, 56.99; H, 6.27; N, 4.36; S, 7.48%.

(4) Preparation of 6'-N-benzyloxycarbonyl-1,3,3''-tri-N-tosyl-5,2'-O-isopropylidene-4'',6''-O-cyclohexylidene-2''-O-tetrahydropyranyl-3',4'-di-O-benzylsulfonyl-kanamycin A The product of the above procedure (3), namely 6'-N-benzyloxycarbonyl-4'',6''-O-cyclohexylidene-5,2'-O-isopropylidene-2''-O-tetrahydropyranyl-1,3,3''-tri-N-tosyl-kanamycin A (519 mg) in 10 ml of pyridine was cooled with ice, and the ice-cooled solution was admixed with 164 mg of benzylsulfonyl chloride. The resulting admixture continued to be ice-cooled for 1 hour for the 3',4'-di-O-benzylsulfonylation. The reaction solution was admixed with 0.1 ml of water and then concentrated, and the concentrated solution was further admixed with a volume of water to deposit a solid. This solid was removed by filtration, well washed with water and dried, affording 618 mg (96%) of the above titled compound as a colorless solid. $[\alpha]_D^{25} +39°$ (c 1, chloroform).

Elemental analysis Found: C, 56.21; H, 5.88; N, 3.38; S, 9.80%. Calcd. (for $C_{75}H_{92}N_4O_{24}S_5$): C, 56.52; H, 5.82; N, 3.52; S, 10.06%.

(5) Preparation of 6'-N-benzyloxycarbonyl-1,3,3''-tri-N-tosyl-3',4'-dideoxy-3'-eno-kanamycin A The kanamycin A derivative (618 mg) obtained in the above procedure (4) was heated in 10 ml of 80% aqueous acetic acid for 1 hour at 80° C. to remove the hydroxyl-protecting groups, the isopropylidene group, cyclohexylidene group and tetrahydropyranyl group therefrom. The reaction mixture was then concentrated to a smaller volume, followed by addition of water to the resulting concentrated solution to deposit a solid. This solid was removed by filtration, washed with water and dried to afford 541 mg (100%) of the de-isopropylidenated, de-cyclohexylidenated and de-tetrahydropyranylated product, that is, 6'-N-benzyloxycarbonyl-1,3,3''-tri-N-tosyl-3',4'-di-O-benzylsulfonyl-kanamycin A in the form of a colorless solid. This substance (339 mg) was taken up into 7 ml of dimethylformamide, and the resulting solution was admixed with 3.5 g of sodium iodide and 1.8 g of zinc metal powder, followed by heating at 100° C. for 1 hour under stirring to effect the reaction for the formation of the 3'-eno-kanamycin A derivative. The reaction mixture was admixed with a large volume of chloroform to deposit the excessive quantity of sodium iodide. The admixture was centrifuged to remove the sodium iodide precipitate, and the organic solvent solution (the supernatant) so obtained was concentrated to dryness in vacuo. The solid residue was dissolved in 15 ml of chloroform and the solution was chromatographed for the purification of the kanamycin A derivative by passing through a column of silica gel and developing the column with chloroform-methanol (8:1) as the eluent. The eluate containing the aimed compound, that is, 6'-N-benzyloxycarbonyl-1,3,3''-tri-N-tosyl-3',4'-dideoxy-3'-eno-kanamycin A was concentrated to dryness in vacuo to give the above titled product as a colorless solid. Yield 203 mg (80%). $[\alpha]_D^{25} +15°$ (c 1, chloroform).

Elemental analysis Found: C, 52.92; H, 5.48; N, 5.18; S, 8.87%. Calcd. (for $C_{47}H_{58}N_4O_{17}S_3 \cdot H_2O$): C, 52.99; H, 5.68; N, 5.26; S, 9.03%.

(6) Production of 3',4'-dideoxykanamycin A

The kanamycin A derivative (203 mg) obtained in the above procedure (5) was dissolved in 2 ml of dioxane, followed by the treatment with hydrogen in the same manner as in the above Example 1 (8) in the presence of platinum oxide (20 mg) added to effect the hydrogenation of the 3',4'-olefinic bond and the concurrent removal of the 6'-N-benzyloxycarbonyl group. A crude product of 1,3,3''-tri-N-tosyl-3',4'-dideoxykanamycin A was obtained in a yield of 204 mg (100%).

This tri-N-tosyl-3',4'-dideoxykanamycin A compound was dissolved in about 100 ml of liquid ammonia at $-50°$ C., to which were then added 300 mg of sodium metal pieces. The admixture was subjected to the reaction of removing the tri-N-tosyl groups in the same manner as in the above Example 1 (8), followed by the procedure of purification in the same way as in the above Example 1 (8). A purified product of 3',4'-dideoxykanamycin A was obtained in a yield of 67.9 mg (67%).

EXAMPLE 3

Synthesis of 3',4'-dideoxykanamycin A (1) Preparation of 6'-N-benzyloxycarbonyl-1,3,3''-tri-N-tosyl-5,2'-O-isopropylidene-4'',6''-O-cyclohexylidene-2''-O-tetrahydropyranyl-3',4'-di-O-methanesulfonylkanamycin A The protected kanamycin A derivative obtained in the above Example 2 (3), that is, the 6'-N-benzyloxycarbonyl-4'',6''-O-cyclohexylidene-5,2'-O-isopropylidene-2''-O-tetrahyropyranyl-1,3,3''-tri-N-tosyl-kanamycin A (640 mg) was taken up into 10 ml of pyridine, and the resulting solution after ice-cooling was admixed with 135 mg of methanesulfonyl chloride, followed by agitation for 1 hour under ice-cooling to effect the 3',4'-di-O-methanesulfonylation. The reaction mixture, after addition of 0.1 ml of water thereto, was concentrated to a smaller volume and then diluted with water to deposit a solid which was subsequently removed by filtration, well washed with water and dried. The above titled compound was afforeded as a colorless solid in a yield of 680 mg (95%). $[\alpha]_D^{25} +43°$ (c 1, chloroform).

Elemental analysis Found: C, 52.41; H, 5.63; N, 3.67; S, 10.88%. Calcd. (for $C_{63}H_{84}N_4O_{24}S_5$): C, 52.48; H, 5.87; N, 3.89; S, 11.12%.

(2) Preparation of 6'-N-benzyloxycarbonyl-1,3,3''-tri-N-tosyl-3',4'-dideoxy-3'-eno-kanamycin A The 3',4'-di-O-methanesulfonyl-kanamycin A derivative (563 mg) obtained in the above procedure (2) was heated in 10 ml of 80% aqueous acetic acid at 80° C. for 1 hour to remove the hydroxyl-protecting groups, the isopropylidene group, cyclohexylidene group and tetrahydropyranyl group therefrom. The reaction mixture was concentrated to a smaller volume, and the concentrated solution was admixed with a volume of water to deposit a solid. This solid was collected by filtration, washed with water and dried to afford 510 mg of a partially deprotected kanamycin A derivative, that is, 6'-N-benzyloxycarbonyl-1,3,3''-tri-N-tosyl-3',4'-di-O-methanesulfonyl-kanamycin A. This substance was dissolved in 7 ml of dimethylformamide, and the resulting solution was admixed with 3.5 g of sodium iodide and 1.8 g of zinc methal powder, followed by heating for 1 hour at 100° C. to effect the reaction of forming the 3'-eno-kanamycin A derivative. The reaction mixture obtained was admixed with a large volume of chloroform, and the sodium iodide so precipitated was removed from the organic liquid phase by centrifugation. The organic liquid phase was concentrated to dryness in vacuo, and the residual solid was purified by subjecting a solution of it in chloroform to a chromatography on silica gel column developed with chloroform-methanol (8:1). The above titled compound was afforded as a colorless solid in a yield of 317 mg (76%). $[\alpha]_D^{25} +15°$ (c 1, chloroform).

Elemental analysis Found: C, 52.92; H, 5.48; N, 5.18; S, 8.87%. Calcd. (for $C_{47}H_{58}N_4O_{17}S_3 \cdot H_2O$): C, 52.99; H, 5.68; N, 5.26; S, 9.03%.

(3) Production of 3',4'-dideoxykanamycin A

The protected 3'-eno-kanamycin A derivative obtained in the above procedure (2) was subjected to the catalytic hydrogenation with hydrogen and also to the treatment with sodium metal in liquid ammonia in the same manner as described in the above Example 2 (6) to give 3',4'-dideoxykanamycin A. Yield 101 mg (65%).

EXAMPLE 4

Synthesis of 1-N-((S)-2-hydroxy-4-aminobutyryl)-3',4'-dideoxykanamycin A (1) preparation of 3,6'-di-N-benzyloxycarbonyl-3',4'-dideoxykanamycin A The 3',4'-dideoxykanamycin A carbonate obtained in the Example 1 given hereinbefore was dissolved in 8 N aqueous ammonia, and the resulting aqueous solution was concentrated to dryness in vacuo while said solution was prevented from contacting with the carbon dioxide component present in the air. In this way, the free base form of 3',4'-dideoxykanamycin A was prepared. This 3',4'-dideoxykanamycin A (free base) (85.4 mg) was suspended in 1.3 ml of dimethylsulfoxide, followed by addition of zinc acetate di-hydrate ($Zn(CH_3CO_2)_2 \cdot 2H_2O$) (187 mg) to the resulting suspension. Into the reaction vessel containing said suspension was introduced a stream of nitrogen gas to replace the air in the reaction vessel by nitrogen gas. The reaction vessel was then sealed and the suspension was agitated at ambient temperature for 3 hours until the suspension became a homogeneous solution containing the complex of zinc acetate with 3',4'-dideoxykanamycin A so formed. To this homogenous solution was added slowly and in small portions 90 mg of N-benzyloxycarbonyloxy-succinimide in 2 hours. Ethyl ether (5 ml) was added to the admixture, which was then shaken vigorously and left to stand for a while. The supernatant solution was separated by decantation from the lower syrupy phase which was containing the complex of zinc acetate with the N-benzyloxycarbonylated 3',4'-dideoxykanamycin A. The lower syrupy phase was again admixed with 5 ml of ethylether, shaken vigorously, left to stand and then separated from the supernatant solution. The lower syrupy phase so freshly formed was subjected further 4 times to the treatment with ethyl ether in the same manner as above. A thick syrupy solid (ca. 450 mg) was obtained, which was supported to be a mixture of 3,6'-di-N-benzyloxycarbonyl-3',4'-dideoxykanamycin A, its zinc acetate complex, zinc acetate and the solvent used. This thick, syrupy solid was dissolved in 30 ml of water-dioxane (1:1), followed by a chromatographic separation on a column of CM-Sephadex C-25 developed with water-dioxane (1:1) containing 0.1 N ammonia, during which the zinc acetate complex of 3',4'-dideoxykanamycin A as N-benzyloxycarbonylated was decomposed to isolate 3,6'-di-N-benzyloxycarbonyl-3',4'-dideoxykanamycin A. The eluate from the CM-Sephadex column containing the substance positive to the ninhydrin reaction was concentrated to dryness in vacuo. The above titled compound was afforded as a colorless solid in a yield of 113 mg (83%). $[\alpha]_D^{25} +77°$ (c 1, water-dimethylformamide=1:2).

(2) 1-N-acylation of 3,6'-di-N-benzyloxycarbonyl-3',4'-dideoxykanamycin A

The N-protected 3',4'-dideoxykanamycin A derivative (113 mg) obtained in the above procedure (1) was dissolved in 2 ml of water-dioxane (1:1), and to the resulting solution were added 6.8 mg of anhydrous sodium carbonate and then slowly in 2 hours 59.4 mg of N-hydroxysuccinimide ester (as an active ester) of (S)-2-hydroxy-4-benzyloxycarbonylamino-butyric acid

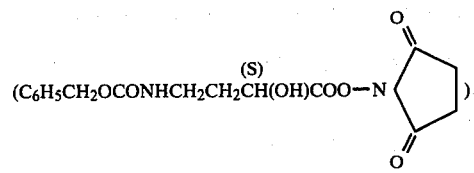

at ambient temperature under stirring. The admixture was allowed to stand for 1 hour at ambient temperature, and the reaction mixture so formed was concentrated to dryness in vacuo. The residual solid was admixed with a volume of water and the water-insoluble solid matter was separated from the aqueous phase and dried (121 mg). This water-insoluble solid was mainly comprising 1-N-((S)-2-hydroxy-4-N-benzyloxycarbonylaminobutyryl)-3,6'-di-N-benzyloxycarbonyl-3',4'-dideoxykanamycin A formed.

(3) Removal of the amino-protecting benzyloxycarbonyl groups

The water-insoluble solid obtained in the above procedure (2) was taken up into a mixture of dioxane (2 ml), water (0.5 ml) and acetic acid (0.05 ml), and the resulting solution was shaken under hydrogen gas at 1 atm. for 1 hour at ambient temperature in the presence of 10 mg of palladium-black added thereto to effect the removal of the benzyloeycarbonyl groups by the catalytic hydrogenolysis. The reaction solution was filtered to remove the catalyst, and the filtrate was concentrated to dryness in vacuo. The residual solid obtained was dissolved in 1 ml of water, followed by gradient chromatography on a column of CM-Sephadex C-25 developed with water containing 0→0.5 N ammonia. The eluate from the CM-Sephadex column containing the desired product were concentrated to dryness in vacuo. The desired 1-N-((S)-2-hydroxy-4-aminobutyryl)-3',4'-dideoxykanamycin A was obtained as the mono-carbonate in the form of a colorless solid. Yield 32 mg (33% calculated as the mono-carbonate). $[\alpha]_D^{25} +91°$ (c 1, water).

EXAMPLE 5

Synthesis of 1-N-(DL-2-hydroxy-3-aminopropionyl)-3',4'-dideoxykanamycin A

The N-protected 3',4'-dideoxykanamycin A obtained in the above Example 4 (1), that is, 3,6'-di-N-benzyloxycarbonyl-3',4'-dideoxykanamycin A (120 mg) was dissolved in 2 ml of water-dioxane (1:1), and the resulting solution was admixed with 7 mg of anhydrous sodium carbonate and then with 60 mg of N-hydroxysuccinimide ester of DL-2-hydroxy-3-benzyloxycarbonylaminopropionic acid

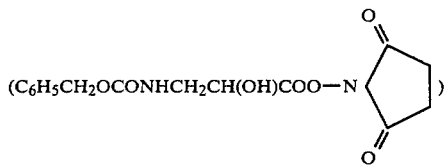

in the same way as in the above Example 4 (2). The admixture so obtained was subsequently treated entirely in the same manner as in the Example 4 (2) and further subjected to the catalytic hydrogenolysis in the above Example 4 (3). The above titled compound in the form of a mono-carbonate was afforded as a colorless solid in a yield of 42 mg (42% calculated as the mono-carbonate). $[\alpha]_D^{25} +93°$ (c 1, water).

We claim:

1. A compound which is 3',4'-dideoxykanamycin A of the formula

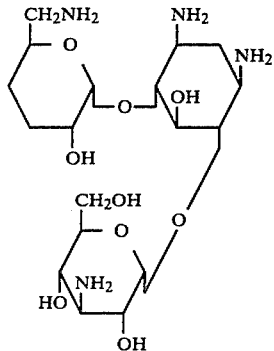

or a pharmaceutically acceptable acid-addition salt thereof.

2. A compound which is 1-N-(2-hydroxy-3-aminopropionyl)-3',4'-dideoxykanamycin A or 1-N-(2-hydroxy-4-aminobutyryl)-3',4'-dideoxykanamycin A represented by the general formula

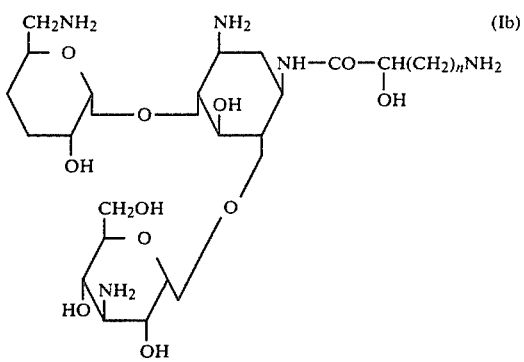

wherein n is an integer of 1 or 2, or a pharmaceutically acceptable acid-addition salt thereof.

3. A compound which is 1-N-(DL-2-hydroxy-3-aminopropionyl)-3',4'-dideoxykanamycin A or a pharmaceutically acceptable acid-addition salt thereof.

4. A compound which is 1-N-((S)-2-hydroxy-4-aminobutyryl)-3',4'-dideoxykanamycin A or a pharmaceutically acceptable acid-addition salt thereof.

5. A compound of the formula

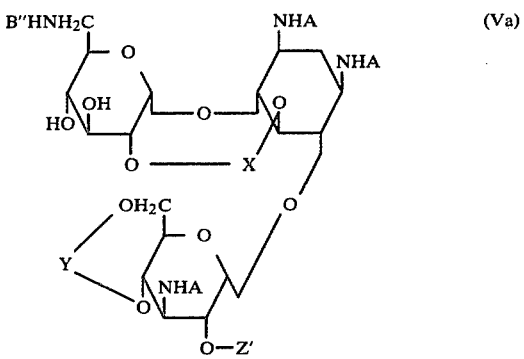

wherein each A represents alkylsulfonyl containing 1 to 4 carbon atoms, tosyl or benzylsulfonyl; B" represents alkoxycarbonyl containing 2 to 5 carbon atoms or benzyloxycarbonyl; X represents isopropylidene, cyclohexylidene, benzylidene or tetrahydro-4-pyranylidene; Y represents alkylidene containing 1 to 6 carbon atoms, cyclohexylidene, benzylidene or tetrahydro-4-pyranylidene; and Z' is hydrogen or tetrahydropyranyl.

6. A compound which is selected from the group consisting of 6'-N-benzyloxycarbonyl-1,3,3"-tri-N-tosyl-5,2'-O-isopropylidene-4",6"-O-cyclohexyliden-kanamycin A and 6'-N-benzyloxycarbonyl-1,3,3"-tri-N-tosyl-5,2'-O-isopropylidene-4",6"-O-cyclohexylidene-2"-O-tetrahydropyranyl-kanamycin A.

* * * * *